(12) United States Patent
Sakakibara et al.

(10) Patent No.: US 8,124,834 B2
(45) Date of Patent: Feb. 28, 2012

(54) USE OF ACTIVE CYTOKININ SYNTHASE GENE

(75) Inventors: Hitoshi Sakakibara, Kanagawa (JP); Nanae Ueda, Kanagawa (JP); Takeshi Kuroha, Kanagawa (JP)

(73) Assignee: Riken, Wako-shi (JP)

( * ) Notice: Subject to any disclaimer, the term of this patent is extended or adjusted under 35 U.S.C. 154(b) by 508 days.

(21) Appl. No.: 12/281,238

(22) PCT Filed: Sep. 4, 2007

(86) PCT No.: PCT/JP2007/067558
§ 371 (c)(1),
(2), (4) Date: Aug. 29, 2008

(87) PCT Pub. No.: WO2008/029942
PCT Pub. Date: Mar. 13, 2008

(65) Prior Publication Data
US 2009/0317863 A1    Dec. 24, 2009

(30) Foreign Application Priority Data
Sep. 4, 2006  (JP) .................................. 2006-238691

(51) Int. Cl.
*C12N 15/82* (2006.01)
(52) U.S. Cl. .......................................... 800/278; 435/468
(58) Field of Classification Search ........................ None
See application file for complete search history.

(56) References Cited

U.S. PATENT DOCUMENTS

2004/0216190 A1* 10/2004 Kovalic ........................ 800/289
2006/0123505 A1   6/2006 Kikuchi et al.

FOREIGN PATENT DOCUMENTS

| EP | 1 586 645 A2 | 10/2005 |
| WO | WO 02/10210 A2 | 2/2002 |
| WO | WO 03/000898 A1 | 1/2003 |

OTHER PUBLICATIONS

Sasaki T. et al. The genome sequence and structure of rice chromosome I, Nature, 2002, vol. 420, No. 6913, p. 312-316, Accession No. BAD52880, Database:UniProtKB/TrEMBL, Definition:lysine decarboxylase-like protein [Oryza sativa (japonica cultivar-group)].*
Kikuchi S. et al. Collection, mapping, and annotation of over 28,000 cDNA clones from japonica rice., Science, 2003, vol. 301, No. 5631, p. 376-379., Accession No. AK071695, Database:DDBJ/EMBL/GenBank, Definition:Oryza sativa (japonica cultivar-group) cDNA clone:J023109F04, full insert sequence.*
Kiran N.S. et al. Ectopic over-expression of the maize beta-glucosidase Zm-p60.1 perturbs cytokinin homeostasis in transgenic tobacco. J Exp Bot. 2006;57(4):985-96. Epub Feb. 17, 2006.*
Carey A.T. at et al. Down-regulation of a ripening-related beta-galactosidase gene (TBG1) in transgenic tomato fruits. J Exp Bot. Apr. 2001;52(357):663-8.*
Temple S.J. et al. Down-regulation of specific members of the glutamine synthetase gene family in alfalfa by antisense RNA technology. Plant Mol Biol. Jun. 1998;37(3):535-47.*
Xiaoying Lin, et al., "Sequence and Analysis of Chromosome 2 of the Plant *Arabidopsis thaliana*", Nature, vol. 402, XP002952930, Dec. 16, 1999, pp. 761-768.
K. Mayer, et al., "Sequence and Analysis of Chromosome 4 of the Plant *Arabidopsis thaliana*", Nature, vol. 402, No. 6763, XP002159526, Dec. 16, 1999, pp. 769-777.
The Kazusa DNA Research Institute, et al., "Sequence and Analysis of Chromosome 5 of the Plant *Arabidopsis thaliana*", Nature, vol. 408, No. 6814, XP002551203, Dec. 14, 2000, pp. 823-826.
M. Salanoubat, et al., "Sequence and Analysis of Chromosome 3 of the Plant *Arabidopsis thaliana*", Nature, vol. 408, XP002194202, Dec. 14, 2000, pp. 820-822.
R. Cheuk, et al., "*Arabidopsis thaliana* At5g11950 Gene, Complete Cds", Database Genbank [Online], Database Accession No. BT006409, XP002551204, Apr. 25, 2003, 3 pages.
Takashi Kurakawa, et al., "The Analysis of LOG Gene, A New Regulator of Meristem Activity in Rice", Plant Cell Physiology, vol. 46, Supplement, 087(1pB12), XP009124193, 2005, p. S46.
Sasaki T. et al., "The genome sequence and structure of rice chromosome 1", Nature, vol. 420, No. 21, pp. 312-316, (2002).

(Continued)

*Primary Examiner* — Cynthia Collins
(74) *Attorney, Agent, or Firm* — Oblon, Spivak, McClelland, Maier & Neustadt, L.L.P.

(57) ABSTRACT

It is an object of the present invention to clarify an enzyme gene capable of directly regulating the amount of active cytokinins synthesized and to provide a transformed plant with a regulated amount of cytokinins using the aforementioned gene.

The present invention provides a transformed plant into which a gene defined in any one of the following (a) to (d) is introduced:

(a) a gene consisting of a DNA consisting of the nucleotide sequence as shown in any one of SEQ ID NOS: 1, 3, 5, 7, 9, 11, 13 and 15;

(b) a gene consisting of a DNA which hybridizes under stringent conditions to a DNA consisting of a nucleotide sequence complementary to a DNA consisting of the nucleotide sequence as shown in any one of SEQ ID NOS: 1, 3, 5, 7, 9, 11, 13 and 15 and encodes a protein having activity of catalyzing reactions that synthesize active cytokinins from nucleotide cytokinins;

(c) a gene encoding a protein consisting of the amino acid sequence as shown in any one of SEQ ID NOS: 2, 4, 6, 8, 10, 12, 14 and 16; or (d) a gene encoding a protein which consists of an amino acid sequence derived from the amino acid sequence as shown in any one of SEQ ID NOS: 2, 4, 6, 8, 10, 12, 14 and 16 by deletion, substitution or addition of one or several amino acid residues and has activity of catalyzing reactions that synthesize active cytokinins from nucleotide cytokinins.

13 Claims, 19 Drawing Sheets

OTHER PUBLICATIONS

Kikuchi S. et al., "Collection, Mapping, and Annotation of Over 28,000 cDNA Clones from japonica Rice", Science, vol. 301, No. 5631, pp. 376-379, (2003).

Kurakawa T. et al., "The analysis of LOG, a new regulator of shoot apical meristem activity in rice", Plant Cell Physiology, vol. 47, No. Suppl. S, pp. S76, 207, (2006).

Hitoshi S. et al., "Cytokinin no Seigosei to Shinki no Kasseika Keiro", Protein, Nucleic Acid, and Enzyme, vol. 52, No. 11, pp. 1322 to 1329 and 1402, (2007), (with partial English translation).

Ueda N. et al., "Ine Keicho Bunretsu Soshiki Iji ni Kakawaru LOG Idenshi wa Cytokinin Kasseika Koso o Code Shiteiru", Japanese Society of Plant Physiologists, vol. $48^{th}$, p. 194, 3sD01 (405), (2007), (with English abstract).

Kurakawa T. et al., "Direct control of shoot meristem activity by a cytokinin-activating enzyme", Nature, vol. 445, No. 7128, pp. 652-655, (2007).

* cited by examiner

WT

35S::AtLOG7 #26

USE OF ACTIVE CYTOKININ SYNTHASE GENE

CROSS-REFERENCE TO RELATED APPLICATIONS

This application is a 371 of PCT/JP07/67558 filed Sep. 4, 2007 and claims the benefit of JP 2006-238691 filed Sep. 4, 2006.

TECHNICAL FIELD

The present invention relates to use of an active cytokinin synthase gene. More specifically, the present invention relates to a method for producing a transformed plant using an enzyme gene having activity of catalyzing reactions that synthesize active cytokinins from nucleotide cytokinins.

BACKGROUND ART

Cytokinin has various types of physiological activities such as promotion of cell division, regulation of cell cycle, retardation of senescence, or activation of axillary buds outgrowth, and thus it is an extremely important plant hormone for controlling the quantitative productivity of crops.

As a basic structure, cytokinin has a prenyl group containing 5 carbon atoms at the nitrogen atom on the position 6 of adenine. Depending on the difference of a side chain structure, cytokinin includes trans-zeatin (tZ), isopentenyladenine (iP), etc. Based on the findings from conventional studies regarding a cytokinin-metabolizing system, it has been considered that the synthesis of active cytokinin (a base form) is carried out via at least the following 3 steps of reactions. First, in a first reaction of cytokinin synthesis, nucleotide cytokinin is produced as a result of a condensation reaction between adenine nucleotide and dimethylallyl diphosphate (DMAPP). This nucleotide form does not have activity as cytokinin. However, in a second reaction, such nucleotide form is converted to nucleoside cytokinin by the action of dephosphorylating enzyme. Thereafter, ribose is dissociated by the action of nucleosidase, and thus it is converted to an active cytokinin molecule of a base form (Non-Patent Document 1; Review: Sakakibara, H. (2006) Cytokinins: Activity, biosynthesis and translocation. Annu. Rev. Plant Biol. 57: 431-449). As a matter of fact, in a study at an enzyme level in 1980s, enzymes catalyzing each of the aforementioned reactions have been suggested. An enzyme gene (IPT) catalyzing the first reaction (condensation reaction), namely, the synthesis reaction of nucleotide cytokinin, was identified in 2001 (Patent Document 1: WO2002/072818). However, enzyme genes catalyzing the second reaction (activation reaction) consisting of the remaining 2 steps have not yet been identified. Even if the entities of such genes are identified, in order to artificially regulate the amount of cytokinin as a base form generated, two steps, namely, a step of converting a nucleotide form to a nucleoside form and a step of converting the nucleoside form to a base form, must be simultaneously modified. Thus, it is necessary to identify enzyme genes catalyzing the two reactions and then to simultaneously regulates the identified enzyme genes. Such operation is not easy. On the other hand, it is also possible to regulate the amount of active cytokinins by regulating an enzyme gene (CKX) catalyzing a cytokinin-degrading reaction (Non-Patent Document 2: Werner T, Motyka V, Strnad M, Schmulling T. (2001) Regulation of plant growth by cytokinin. Proc Natl Acad Sci USA 98: 10487-10492; Non-Patent Document 3: Ashikari, M., Sakakibara, H., Lin, S.-Y., Yamamoto, T., Takashi, T., Nishimura, A., Angeles, E. R., Qian, Q., Kitano, H. and Matsuoka, M. (2005) Cytokinin oxidase regulates rice grain production, Science, 309: 741-745). However, a technique of directly regulating the amount of active cytokinin synthesized has not yet been developed so far. In addition, the amount of a base form is increased by excessive expression of IPT, but such a method is problematic in that the total amount of cytokinin is extremely increased due to such excessive expression of IPT and the form as a plant body is also significantly changed (Non-Patent Document 4: Zubko E, Adams C J, Machaekova I, Malbeck J, Scollan C, Meyer P. 2002. Activation tagging identifies a gene from *Petunia hybrida* responsible for the production of active cytokinins in plants. Plant J. 29: 797-808).

DISCLOSURE OF THE INVENTION

It is an object of the present invention to clarify an enzyme gene capable of directly regulating the amount of active cytokinins synthesized and to provide a transformed plant with a regulated amount of cytokinins using the aforementioned gene.

The present inventors have conducted intensive studies directed towards achieving the aforementioned object. The inventors have focused on a gene expressing in rice shoot apical meristems and have analyzed the structure and function thereof. Based on database, it had been anticipated that the aforementioned enzyme gene is associated with decarboxylation of lysine. However, as a result of the analysis, the inventors have newly found that the aforementioned gene does not have such lysine decarboxylase activity but it has activity of catalyzing reactions that synthesize active cytokinins from nucleotide cytokinins (a cytokinin activation reaction). Moreover, the inventors have also found that the aforementioned enzyme gene is able to conduct such a cytokinin activation reaction via 1 step, which had previously been considered to be conducted via 2 steps.

The present invention has been completed based on such findings.

That is to say, the present invention includes the following features.

(1) A transformant into which a gene defined in any one of the following (a) to (d) is introduced:

(a) a gene consisting of a DNA consisting of the nucleotide sequence as shown in any one of SEQ ID NOS: 1, 3, 5, 7, 9, 11, 13 and 15;

(b) a gene consisting of a DNA which hybridizes under stringent conditions to a DNA consisting of a nucleotide sequence complementary to a DNA consisting of the nucleotide sequence as shown in any one of SEQ ID NOS: 1, 3, 5, 7, 9, 11, 13 and 15 and encodes a protein having activity of catalyzing reactions that synthesize active cytokinins from nucleotide cytokinins;

(c) a gene encoding a protein consisting of the amino acid sequence as shown in any one of SEQ ID NOS: 2, 4, 6, 8, 10, 12, 14 and 16; or (d) a gene encoding a protein which consists of an amino acid sequence derived from the amino acid sequence as shown in any one of SEQ ID NOS: 2, 4, 6, 8, 10, 12, 14 and 16 by deletion, substitution or addition of one or several amino acid residues and has activity of catalyzing reactions that synthesize active cytokinins from nucleotide cytokinins.

(2) The transformant according to (1) above, which is a transformed plant.

(3) The transformant according to (2) above, wherein the plant is a plant body, a plant organ, a plant tissue, or a cultured plant cell.

(4) A recombinant vector comprising a gene defined in any one of the following (a) to (d):
   (a) a gene consisting of a DNA consisting of the nucleotide sequence as shown in any one of SEQ ID NOS: 1, 3, 5, 7, 9, 11, 13 and 15;
   (b) a gene consisting of a DNA which hybridizes under stringent conditions to a DNA consisting of a nucleotide sequence complementary to a DNA consisting of the nucleotide sequence as shown in any one of SEQ ID NOS: 1, 3, 5, 7, 9, 11, 13 and 15 and encodes a protein having activity of catalyzing reactions that synthesize active cytokinins from nucleotide cytokinins;
   (c) a gene encoding a protein consisting of the amino acid sequence as shown in any one of SEQ ID NOS: 2, 4, 6, 8, 10, 12, 14 and 16; or
   (d) a gene encoding a protein which consists of an amino acid sequence derived from the amino acid sequence as shown in any one of SEQ ID NOS: 2, 4, 6, 8, 10, 12, 14 and 16 by deletion, substitution or addition of one or several amino acid residues and has activity of catalyzing reactions that synthesize active cytokinins from nucleotide cytokinins.

(5) A method for producing a transformed plant, which is characterized in that it comprises introducing a gene defined in any one of the following (a) to (d) or the recombinant vector according to (4) above into a plant cell, and regenerating a plant body from the plant cell:
   (a) a gene consisting of a DNA consisting of the nucleotide sequence as shown in any one of SEQ ID NOS: 1, 3, 5, 7, 9, 11, 13 and 15;
   (b) a gene consisting of a DNA which hybridizes under stringent conditions to a DNA consisting of a nucleotide sequence complementary to a DNA consisting of the nucleotide sequence as shown in any one of SEQ ID NOS: 1, 3, 5, 7, 9, 11, 13 and 15 and encodes a protein having activity of catalyzing reactions that synthesize active cytokinins from nucleotide cytokinins;
   (c) a gene encoding a protein consisting of the amino acid sequence as shown in any one of SEQ ID NOS: 2, 4, 6, 8, 10, 12, 14 and 16; or
   (d) a gene encoding a protein which consists of an amino acid sequence derived from the amino acid sequence as shown in any one of SEQ ID NOS: 2, 4, 6, 8, 10, 12, 14 and 16 by deletion, substitution or addition of one or several amino acid residues and has activity of catalyzing reactions that synthesize active cytokinins from nucleotide cytokinins.

(6) A method for regulating the amount of active cytokinins in a plant, which is characterized in that it comprises controlling the expression level of a gene defined in any one of the following (a) to (d) in the plant:
   (a) a gene consisting of a DNA consisting of the nucleotide sequence as shown in any one of SEQ ID NOS: 1, 3, 5, 7, 9, 11, 13 and 15;
   (b) a gene consisting of a DNA which hybridizes under stringent conditions to a DNA consisting of a nucleotide sequence complementary to a DNA consisting of the nucleotide sequence as shown in any one of SEQ ID NOS: 1, 3, 5, 7, 9, 11, 13 and 15 and encodes a protein having activity of catalyzing reactions that synthesize active cytokinins from nucleotide cytokinins;
   (c) a gene encoding a protein consisting of the amino acid sequence as shown in any one of SEQ ID NOS: 2, 4, 6, 8, 10, 12, 14 and 16; or
   (d) a gene encoding a protein which consists of an amino acid sequence derived from the amino acid sequence as shown in any one of SEQ ID NOS: 2, 4, 6, 8, 10, 12, 14 and 16 by deletion, substitution or addition of one or several amino acid residues and has activity of catalyzing reactions that synthesize active cytokinins from nucleotide cytokinins.

(7) A method for producing active cytokinins, which is characterized in that it comprises culturing the transformant according to (1) above in a medium to which nucleotide cytokinins have been added as substrates, and collecting active cytokinins from the culture.

(8) A method for changing the character of a plant by excessive expression of a gene defined in any one of the following (a) to (d) in the plant body:
   (a) a gene consisting of a DNA consisting of the nucleotide sequence as shown in any one of SEQ ID NOS: 1, 3, 5, 7, 9, 11, 13 and 15;
   (b) a gene consisting of a DNA which hybridizes under stringent conditions to a DNA consisting of a nucleotide sequence complementary to a DNA consisting of the nucleotide sequence as shown in any one of SEQ ID NOS: 1, 3, 5, 7, 9, 11, 13 and 15 and encodes a protein having activity of catalyzing reactions that synthesize active cytokinins from nucleotide cytokinins;
   (c) a gene encoding a protein consisting of the amino acid sequence as shown in any one of SEQ ID NOS: 2, 4, 6, 8, 10, 12, 14 and 16; or
   (d) a gene encoding a protein which consists of an amino acid sequence derived from the amino acid sequence as shown in any one of SEQ ID NOS: 2, 4, 6, 8, 10, 12, 14 and 16 by deletion, substitution or addition of one or several amino acid residues and has activity of catalyzing reactions that synthesize active cytokinins from nucleotide cytokinins.

(9) The method according to (8) above, wherein a change in the character of a plant involves an increase in the number of scapes, formation of large seeds, formation of thick veins, or a change in inflorescence.

Figure 1:
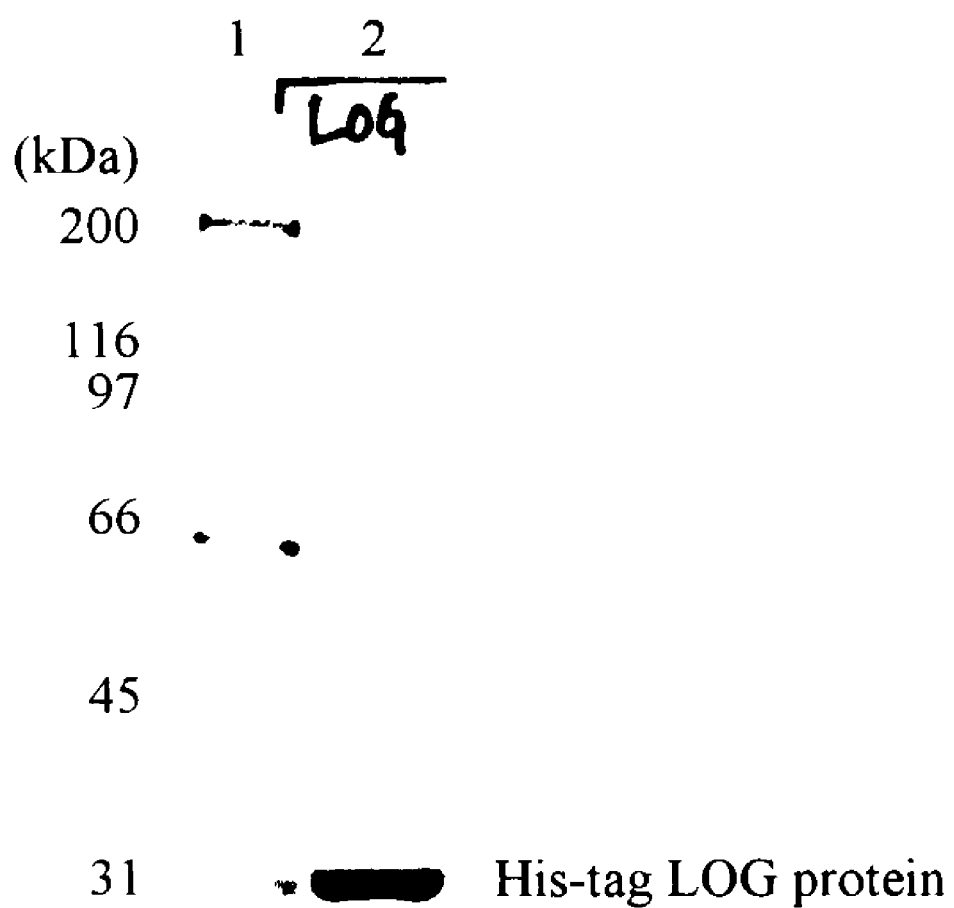
FIG. 1 shows an electrophoretogram of a purified sample of LOG protein (lane 1: a molecular size marker; lane 2: a purified sample of LOG protein (3 μg of protein)).
Figure 2A:
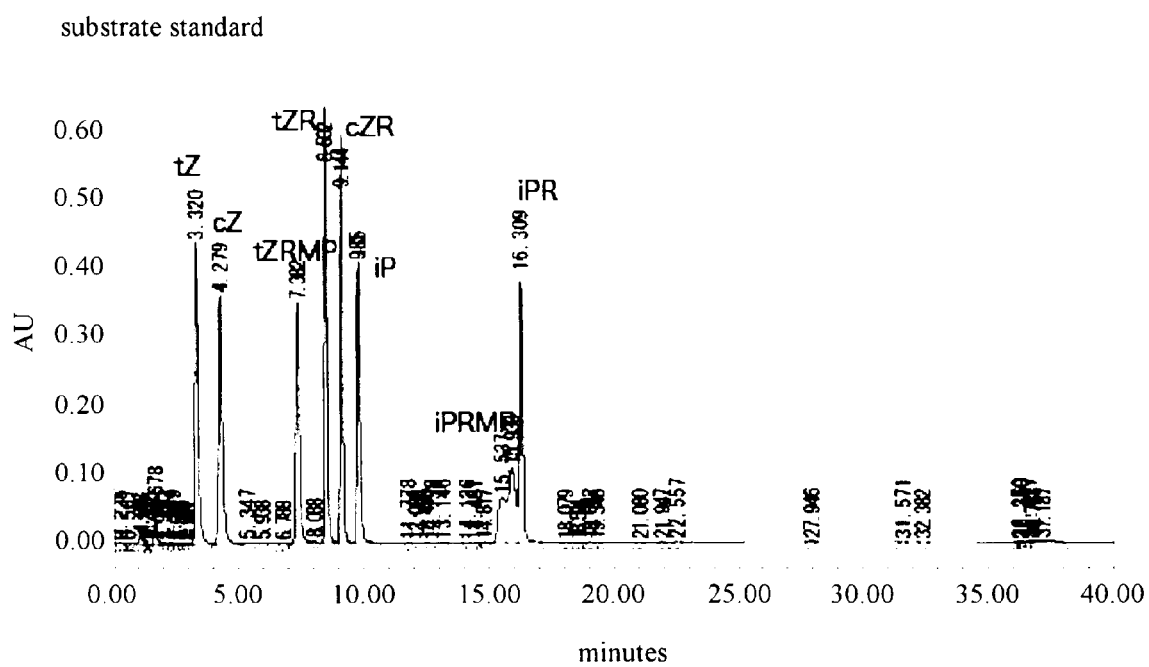
FIG. 2A shows a chromatogram of each substrate sample mixture; and each of FIGS. 2B, 2C and 2D shows a chromatogram of each reaction product obtained by allowing iPRMP (2B), tZRMP (2C) and tZ (2D) used as substrates, to react with a purified LOG protein (upper case: only the substrate; lower case: the reaction product).
Figure 2B:
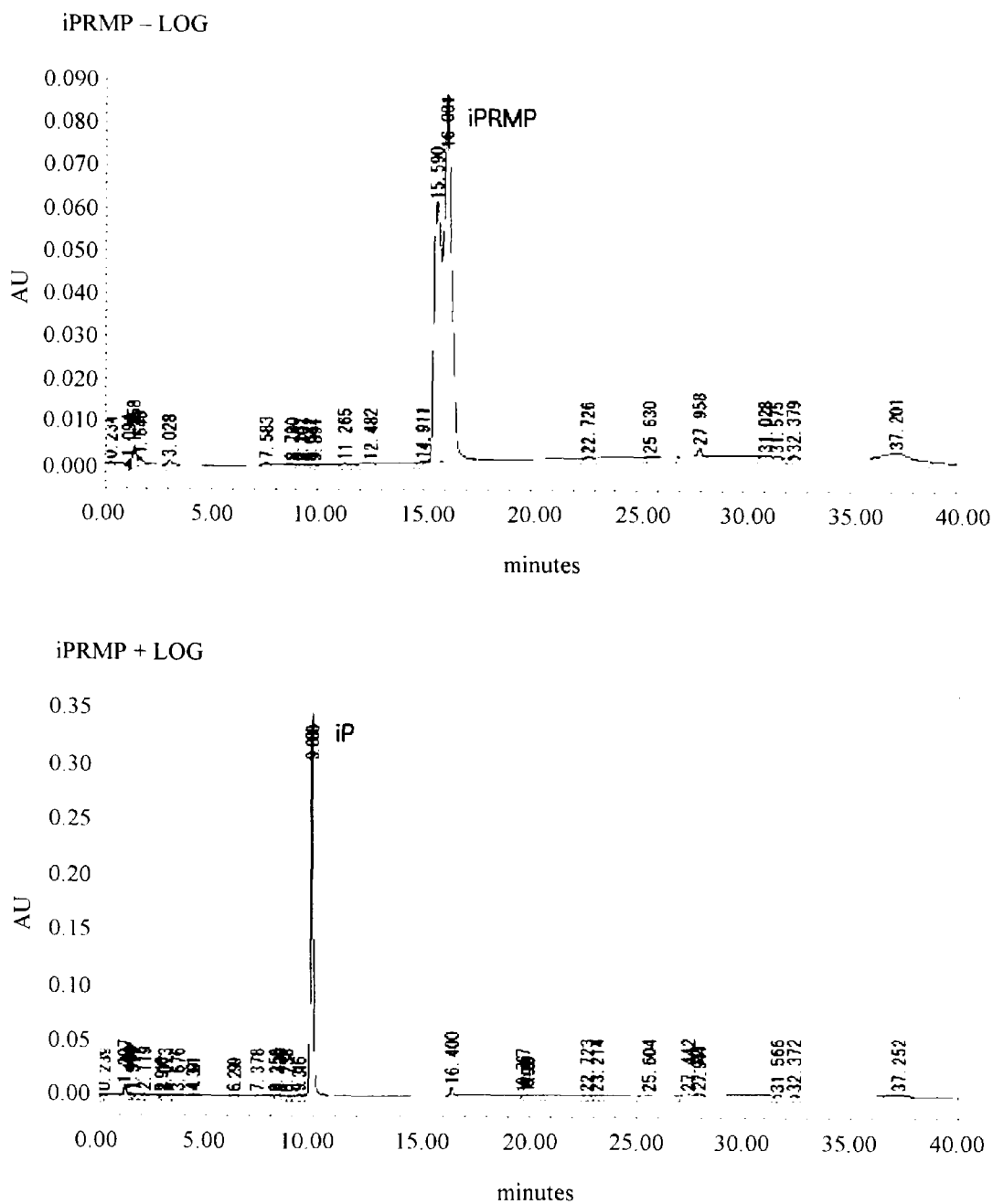
Figure 2C:
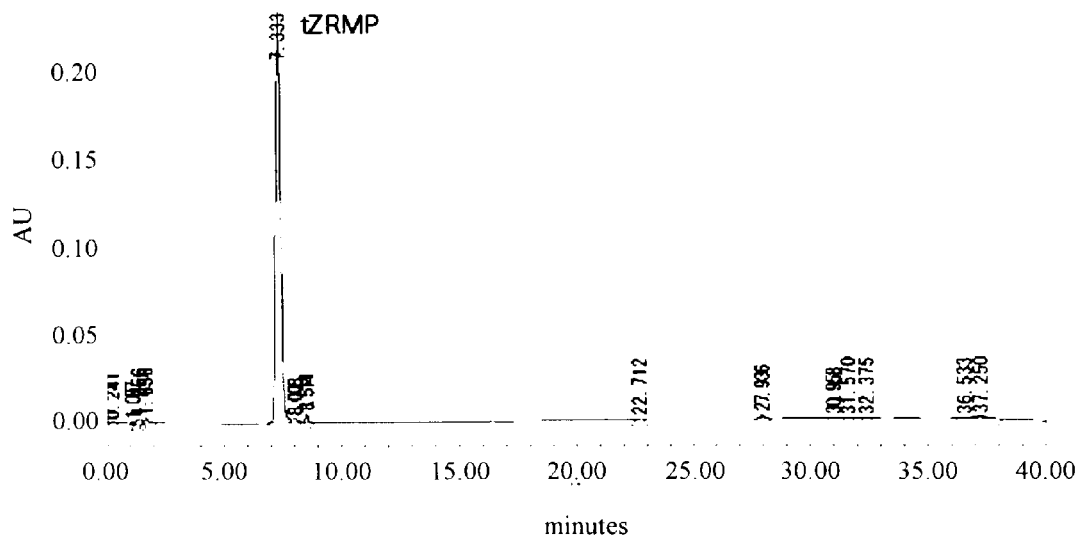
Figure 2C:
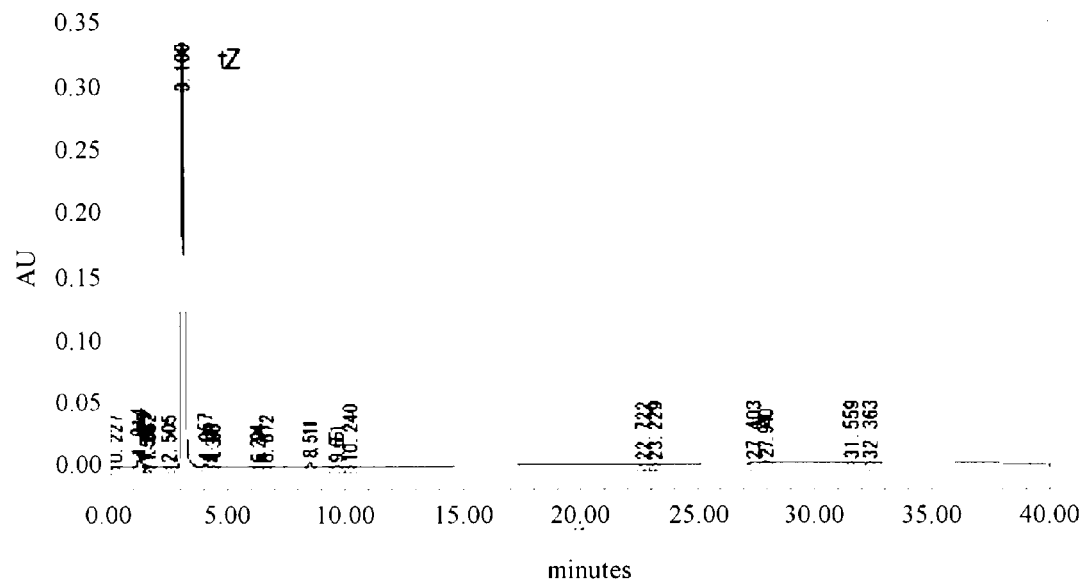
Figure 2D:
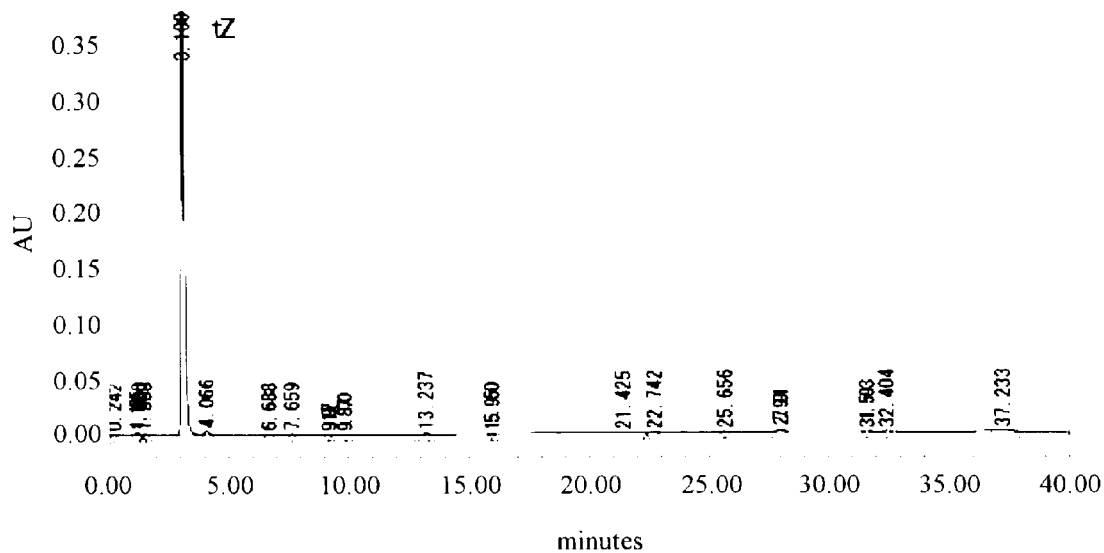
Figure 2D:
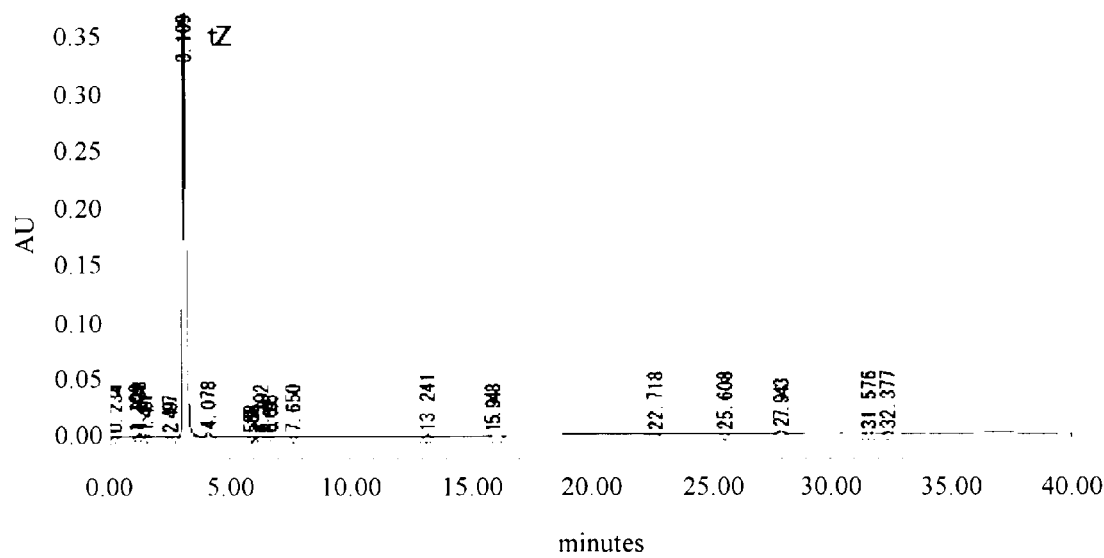

The present application claims priority from Japanese Patent Application No. 2006-238691, filed on Sep. 4, 2006; the disclosure of the specification of which is hereby incorporated by reference.

The present invention will be defined in detail below.

(1) Active Cytokinin Synthase Gene

The present invention relates to use of a gene encoding an enzyme protein having activity of catalyzing reactions that synthesize active cytokinins from nucleotide cytokinins.

The aforementioned gene encoding an enzyme protein having activity of catalyzing reactions that synthesize active cytokinins from nucleotide cytokinins (hereinafter referred to as "LOG gene") is a gene consisting of a DNA having the nucleotide sequence as shown in SEQ ID NO: 1, or a gene encoding a protein consisting of the amino acid sequence as shown in SEQ ID NO: 2. The sequence information of the LOG gene has already been reported in the international nucleotide sequence database (Accession number: AK071695) (nucleotide); BAD52880 (protein); Tigr locus: LOC_Os01g40630; RAP locus: Os01g0588900). It had been estimated from the NCBI database that the protein encoded by the present gene, which consists of 242 amino acids, has a function as a lysine decarboxylase. However, the present inventors have considered that, since the LOG gene is expressed in an undifferentiated cell group called stem cells existing at the tip of rice shoot apical meristems and in the peripheral tissues thereof, this gene is likely to associated with the maintenance of the rice shoot apical meristems. Thus, the inventors have analyzed the functions of the gene. As a result, they have newly found that the aforementioned gene does not have lysine decarboxylase activity, but that it has activity of catalyzing reactions that synthesize active cytokinins from nucleotide cytokinins.

The LOG gene used in the present invention may be a gene encoding a protein which consists of an amino acid sequence derived from the amino acid sequence as shown in SEQ ID NO: 2 by deletion, substitution or addition of one or several amino acid residues, as long as it maintains activity of catalyzing reactions that synthesize active cytokinins from nucleotide cytokinins.

The number of the amino acids that may be deleted, substituted or added is preferably one to several. For example, 1 to 10, and preferably 1 to 5, amino acids may be deleted from the amino acid sequence as shown in SEQ ID NO: 2; 1 to 10, and preferably 1 to 5, amino acids may be added to the amino acid sequence as shown in SEQ ID NO: 2; or 1 to 10, and preferably 1 to 5, amino acids may be substituted with other amino acids in the amino acid sequence as shown in SEQ ID NO: 2.

Moreover, the LOG gene used in the present invention may be a gene encoding a protein which consists of an amino acid sequence having 80% or higher homology to the amino acid sequence as shown in SEQ ID NO: 2 and has activity of catalyzing reactions that synthesize active cytokinins from nucleotide cytokinins. The aforementioned 80% or higher homology preferably refers to homology of 90% or higher, and more preferably to homology of 95% or higher.

The term "activity of catalyzing reactions that synthesize active cytokinins from nucleotide cytokinins" is used herein to mean "activity of catalyzing reactions that eliminates ribose 5'-monophosphates from nucleotide cytokinins and synthesizes the active cytokinins of base forms."

In the present invention, the "nucleotide cytokinins" include isopentenyladenine riboside 5'-monophosphate (iPRMP), trans-zeatin riboside 5'-monophosphate (tZRMP), dihydrozeatin riboside 5'-monophosphate (DZRMP) and cis-zeatin riboside 5'-monophosphate (cZRMP). On the other hand, the "active cytokinins" include $N^6$-(delta-2-isopentenyl)adenine (iP), trans-zeatin (tZ), dihydrozeatin (DZ) and cis-zeatin (cZ), which are produced by eliminating ribose 5'-monophosphate from each of the aforementioned nucleotide cytokinins.

Furthermore, the expression "having activity of catalyzing reactions that synthesize active cytokinins from nucleotide cytokinins" is used to mean that the aforementioned activity is substantially equivalent to the activity of the protein having the amino acid sequence as shown in SEQ ID NO: 2.

The LOG gene of the present invention may also be a gene consisting of a DNA which hybridizes under stringent conditions to a DNA consisting of a nucleotide sequence complementary to a DNA consisting of the nucleotide sequence as shown in SEQ ID NO: 1, and encodes a protein having activity of catalyzing reactions that synthesize active cytokinins from nucleotide cytokinins.

The term "stringent conditions" refers to conditions where what is called a specific hybrid is formed but a non-specific hybrid is not formed. Examples of such stringent conditions include conditions wherein complementary strands of a DNA consisting of a highly homologous nucleic acid, i.e., a DNA consisting of a nucleotide sequence exhibiting 80% or higher, preferably 90% or higher, and more preferably 95% or higher homology to the nucleotide sequence as shown in SEQ ID NO: 1 hybridize, but wherein complementary strands of a nucleic acid having homology lower than the aforementioned level do not hybridize. More specific conditions consist of: a sodium salt concentration of 15 mM to 750 mM, preferably 50 mM to 750 mM, and more preferably 300 mM to 750 mM; a temperature of 25° C. to 70° C., preferably 50° C. to 70° C., and more preferably 55° C. to 65° C.; and a formamide concentration of 0% to 50%, preferably 20% to 50%, and more preferably 35% to 45%. Further, under more stringent conditions, as conditions for washing a filter after hybridization, a sodium salt concentration is generally 15 mM to 600 mM, preferably 50 mM to 600 mM, and more preferably 300 mM to 600 mM, and a temperature is 50° C. to 70° C., preferably 55° C. to 70° C., and more preferably 60° C. to 65° C.

The LOG gene used in the present invention can be obtained in the form of a nucleic acid fragment by performing PCR amplification using primers designed based on the sequence as shown in SEQ ID NO: 1 or 2, and also using, as a template, nucleic acid derived from a cDNA library, a genome DNA library, etc. Also, the LOG gene can be obtained in the form of a nucleic acid fragment by performing hybridization using, as a template, nucleic acid derived from the aforementioned library or the like, and also using, as a probe, a DNA fragment that is a portion of the LOG gene. Otherwise, the LOG gene may also be synthesized in the form of a nucleic acid fragment by various types of nucleic acid sequence synthesis methods known in the present technical field, such as a chemical synthesis method.

The aforementioned deletion, addition, and substitution of amino acids can be carried out by modifying the aforementioned protein-encoding gene via a technique known in the art. Mutation can be introduced to a gene via conventional techniques such as the Kunkel method or the Gapped duplex method, or via techniques equivalent thereto. For example, mutation is introduced using a mutagenesis kit that utilizes site-directed mutagenesis (e.g. a Mutant-K (manufactured by TAKARA) or Mutant-G (manufactured by TAKARA)), or the Takara LA PCR in vitro Mutagenesis series kit.

Furthermore, the LOG gene that can be used in the present invention also includes the following group of genes, which are anticipated to belong to the same gene family, to which the aforementioned LOG gene (Accession number: AK071695) belongs. These genes are also included in the LOG gene of the present invention.

*Arabidopsis thaliana*

| AGI code | Nuc Accession |
| --- | --- |
| At1g50575 | NM_103939 |
| At2g28305 | NM_128389 |
| At2g35990 | NM_129158 |
| At2g37210 | NM_129277 |
| At3g53450 | NM_115205 |
| At5g03270 | NM_120405 |
| At5g06300 | NM_120713 |
| At5g11950 | NM_203039 |
| At4g35190 | NM_119685 |
| At5g26140 | NM_122515 |

*Oryza sativa* (rice)

| tigr locus | NUC accession | protein accession |
| --- | --- | --- |
| LOC_Os01g40630 | AP003243 | BAD52880 |
| LOC_Os01g51210 | AP003273 | NP_916572 |
| LOC_Os02g41770 | AP005000 | XP_473199 |
| LOC_Os03g01880 | XM_468563 | XP_468563 |
| LOC_Os03g49050 | AC123974 | XP_469379 |
| LOC_Os03g64070 | AC096690 | XP_470489 |
| LOC_Os04g43840 | AL731629 | XP_473199 |
| LOC_Os05g51390 | AC136216 | XP_476015 |
| LOC_Os05g46360 | AC104713 | XP_475809 |
| LOC_Os09g37540 | AP005862 | BAD46468 |
| LOC_Os10g33900 | AC037425 | NP_922006 |
| LOC_Os03g39010 | AC133003 | AAT76323 |

Among the aforementioned group of genes, 7 genes, namely, At2g28305, At2g35990, At2g37210, At3g53450, At4g35190, At5g06300 and At5g11950 are *Arabidopsis thaliana* LOG homolog genes (which are referred to as AtLOG 1, 2, 3, 4, 5, 7 and 8, respectively) that encode amino acid sequences showing high homology to the amino acid sequences of the aforementioned *Oryza sativa* LOG proteins. As described in examples given later, as with the aforementioned *Oryza sativa* LOG proteins, these *Arabidopsis thaliana* LOG homolog genes have activity of catalyzing reactions that synthesize active cytokinins from nucleotide cytokinins. Moreover, in a plant wherein the aforementioned gene has been excessively expressed, changes in the character of the plant due to an increase in the amount of active cytokinins synthesized, such as promotion of extension of lateral buds, were observed. The nucleotide sequence of the AtLOG 1, 2, 3, 4, 5, 7 and 8 genes are as shown in SEQ ID NOS: 3, 5, 7, 9, 11, 13 and 15, respectively. These encode the amino acid sequences as shown in SEQ ID NOS: 4, 6, 8, 10, 12, 14 and 16, respectively. In addition, these *Arabidopsis thaliana* LOG homolog genes may also be mutant genes, as long as they have activity of catalyzing reactions that synthesize active cytokinins from nucleotide cytokinins. The range of the sequence homology, and the range of the number of amino acids deleted, substituted or added are as described above.

(2) Recombinant Vectors Used in Transformation of Plants

The recombinant vector of the present invention used in transformation of plants can be constructed by introducing the aforementioned LOG gene into a suitable vector. For example, pBI, pPZP, and pSMA vectors that can introduce a target gene into a plant via *Agrobacterium* are preferably used. A pBI binary vector or an intermediate vector is particularly preferable and examples thereof include pBI121, pBI101, pBI101.2, and pBI101.3. A binary vector is a shuttle vector that can be replicated in *Escherichia coli* and in *Agro-* bacterium. When Agrobacterium containing a binary vector is allowed to infect plants, a DNA in the portion sandwiched between border sequences consisting of the LB sequence and the RB sequence on the vector can be incorporated into the plant nuclear DNA. In contrast, a pUC vector can directly introduce a gene into plants. Examples thereof include pUC18, pUC19, and pUC9 vectors. Plant virus vectors, such as cauliflower mosaic virus (CaMV), bean golden mosaic virus (BGMV), and tobacco mosaic virus (TMV) vectors, can also be used.

When a binary vector plasmid is used, a target gene is inserted between the border sequences (LB and RB sequences) of the binary vector, and this recombinant vector is then amplified in E. coli. Subsequently, the amplified recombinant vector is introduced into Agrobacterium tumefaciens C58, LBA4404, EHA101, EHA105, Agrobacterium rhizogenes LBA1334, or the like via electroporation or other means, and the aforementioned Agrobacterium is used for genetic transduction of plants.

The target gene is inserted into the vector by first cleaving the purified DNA with adequate restriction enzymes, inserting the cleavage fragment into the restriction site or multicloning site of an adequate vector DNA, and ligating the product to the vector.

The target gene needs to be incorporated into a vector in a manner such that functions of the gene are exhibited. Thus, a promoter, an enhancer, a terminator, a replication origin necessary for use of a binary vector (a replication origin derived from a Ti or Ri plasmid, etc.), a selective marker gene, etc. can be ligated to the vector at a site upstream, inside, or downstream of the target gene.

It is possible that the "promoter" not be derived from plants, as long as the DNA can function in plant cells and can induce expression in a specific plant tissue or during a specific growth phase. Specific examples thereof include a rice LOG gene promoter itself, a cauliflower mosaic virus (CaMV) 35S promoter, a nopalin synthase gene promoter (Pnos), a maize ubiquitin promoter, a rice actin promoter, and a tobacco PR protein promoter.

An example of an enhancer is an enhancer region that is used for improving the expression efficiency of the target gene and that comprises the upstream sequence in the CaMV 35S promoter.

Any terminator can be used as long as it can terminate transcription of the gene transcribed by a promoter. Examples thereof include a nopalin synthase (NOS) gene terminator, an octopine synthase (OCS) gene terminator, and a CaMV 35S RNA gene terminator.

Examples of a selective marker gene include an ampicillin resistant gene, a neomycin resistant gene, a hygromycin resistant gene, a bialaphos resistant gene, and a dihydrofolate reductase gene.

Moreover, the selective marker gene and the target gene may be ligated to the same plasmid to prepare a recombinant vector. Alternatively, a recombinant vector that is obtained by ligating the selective marker gene to a plasmid may be prepared separately from a recombinant vector that is obtained by ligating the target gene to a plasmid. When recombinant vectors are separately prepared, both vectors are cotransfected into a host.

(3) Transgenic Plants and Production Method Thereof

The transgenic plant of the present invention can be produced by introducing the aforementioned gene or a recombinant vector into a target plant. The term "introduction of a gene" is used in the present invention to mean that a target gene is introduced into the cells of the aforementioned host plant by a known genetic engineering technique, for example, such that it can be expressed therein. The thus introduced gene may be incorporated into the genomic DNA of the host plant, or it may be present in the form of being contained in a foreign vector.

As a method of introducing the aforementioned gene or a recombinant vector into a plant, a variety of reported and established methods may be used, as appropriate. Examples of such methods include the Agrobacterium method, the PEG-calcium phosphate method, electroporation, the liposome method, the particle gun method, and microinjection. The Agrobacterium method may employ a protoplast, a tissue section, or a plant body itself (the in planta method). When a protoplast is employed, the protoplast is cultured together with the Agrobacterium having a Ti plasmid or an Ri plasmid (Agrobacterium tumefaciens or Agrobacterium rhizogenes, respectively), or it is fused with a spheroplasted Agrobacterium (the spheroplast method). When a tissue section is employed, Agrobacterium is allowed to infect an aseptically cultivated leaf section (a leaf disc) of a target plant or a callus (undifferentiated cultured cells). When the in planta method that utilizes seeds or plants is employed, i.e., a method that is not carried out via tissue culture with the addition of plant hormones, Agrobacterium can be directly applied to water absorptive seeds, young plants (seedlings), potted plants, and the like. These plant transformation methods can be carried out in accordance with the descriptions of general textbooks such as "New edition, Experimental protocols of model plants, From genetic engineering to genome analysis (2001), edited by Isao Shimamoto & Kiyotaka Okada, Shujunsha.

Whether or not the gene has been incorporated into the plant can be confirmed via PCR, Southern hybridization, Northern hybridization, Western blotting, or other methods. For example, a DNA is prepared from a transgenic plant, LOG gene-specific primers are designed, and PCR is then carried out. After PCR has been carried out, the amplification product is subjected to agarose gel electrophoresis, polyacrylamide gel electrophoresis, or capillary electrophoresis and stained with ethidium bromide, a SYBR Green solution, or the like, thereby detecting the amplification product as a band. Thus, transformation can be confirmed. Alternatively, the amplification product can be detected via PCR with the use of primers that have been previously labeled with a fluorescent dye or the like. Further, the amplification product may be bound to a solid phase such as a microplate to thereby confirm the amplification product via fluorescent or enzyme reactions. Further, a protein is extracted from the plant cells, and it is then fractionated by two-dimensional electrophoresis. Thus, a band of protein encoded by the LOG gene is detected, so as to confirm that the LOG gene introduced into the plant cells has been expressed, namely, that the plant has been transformed. Subsequently, the amino acid sequence at the N-terminus of the detected protein is determined by Edman degradation or the like. Thereafter, whether or not the determined amino acid sequence is identical to the sequence at the N-terminus of SEQ ID NO: 2 is confirmed, thereby further demonstrating transformation of the plant cells.

Alternatively, a variety of reporter genes such as β-glucuronidase (GUS), luciferase (LUC), a green fluorescent protein (GFP), chloramphenicol acetyltransferase (CAT), or β-galactosidase (LacZ) are ligated to the downstream region of the target gene to prepare a vector. Agrobacterium, to which the aforementioned vector has been incorporated, is used to transform a plant in the same manner as described above, and the expression of the reporter gene is assayed. Thus, incorporation of the gene into the plant can be confirmed.

In the present invention, either monocotyledonous plants or dicotyledonous plants may be used for transformation. Examples of such plants include those belonging to: Brassicaceae (such as *Arabidopsis thaliana*, cabbage or rapeseed), Gramineae (such as rice, maize, barley or wheat), Solanaceae (such as tomato, eggplant, potato or tobacco), and Leguminosae (such as soybean, garden pea or bush bean), but examples are not limited thereto.

In the present invention, examples of plant materials to be transformed include: plant organs such as a stem, a leaf, a seed, an embryo, an ovule, an ovary or a shoot apex; plant tissues such as an anther or a pollen, or the sections thereof; undifferentiated calluses; and cultured plant cells such as protoplasts prepared by removing cell walls from the undifferentiated calluses via enzyme processing. When the in planta method is employed, water absorptive seeds or a plant body as a whole can also be used.

The term "transgenic plant" is used in the present invention to mean any one of a plant body as a whole, a plant organ (such as a leaf, a petal, a stem, a root, a grain or a seed), a plant tissue (such as epidermis, phloem, parenchyma, xylem or vascular bundle), and a cultured plant cell (such as a callus).

When cultured plant cells are to be transformed, in order to obtain a transformant from the obtained transformed cells, an organ or individual may be regenerated from the obtained transformed cells via conventional tissue culture techniques. A person skilled in the art can easily carry out such procedures via a common technique that is known as a method of regenerating a plant from plant cells. For example, a plant can be regenerated from plant cells in the following manner.

At the outset, when plant tissues or protoplasts are used as plant materials to be transformed, they are cultured in a callus-forming medium that has been sterilized with the addition of, for example, inorganic elements, vitamins, carbon sources, saccharides as energy sources, or plant growth regulators (plant hormones such as auxin, cytokinin, gibberellin, abscisic acid, ethylene or brassinosteroid), and indeterminately proliferating dedifferentiated calluses are allowed to form (hereafter, this process is referred to as "callus induction"). The thus formed calluses are transferred to a new medium containing plant growth regulators, such as auxin, and then further proliferated (subculture).

Callus induction is carried out in a solid medium such as agar, and subculture is carried out in, for example, a liquid medium. This enables both cultures to be carried out efficiently and in large quantities. Subsequently, the calluses proliferated via the aforementioned subculture are cultured under adequate conditions to induce redifferentiation of organs (hereafter referred to as "induction of redifferentiation"), and a complete plant is finally regenerated. Induction of redifferentiation can be carried out by adequately determining the type and quantity of each ingredient in the medium, such as plant growth regulators such as auxin, and carbon sources, light, temperature, and other conditions. Such induction of redifferentiation results in formation of adventitious embryos, adventitious roots, adventitious buds, adventitious shoots, and the like, which leads to growth into complete plants. Alternatively, such items may be stored in a state that pertains before they become complete plants (e.g., encapsulated artificial seeds, dry embryos, or freeze-dried cells and tissues).

The transgenic plant of the present invention also includes the plant bodies of progenies obtained by sexual reproduction or asexual reproduction of the plant body into which the present gene has been introduced (including plant bodies regenerated from the transformed cells or calluses), and portions of the tissues or organs of the progeny plants (a seed, a protoplast, and the like). The transgenic plant of the present invention can be produced in large quantities by obtaining reproduction materials such as seeds or protoplasts from the bodies of transgenic plants transformed by introduction of LOG genes, and then cultivating or culturing them.

In the thus obtained transgenic plant, the amount of active cytokinins is locally or systemically increased due to expression of the LOG gene. As a result, in the transgenic plant, promotion of extension of lateral buds (inhibition of apical dominance), promotion of seed germination, dormancy breaking, promotion of cell division, promotion of chlorophyll synthesis, antiaging, promotion of the enlargement of fruits, an increase in the number of scapes, formation of large seeds, formation of thick veins, the delay of the aging of leaves, a change in inflorescence, etc. are observed due to the action of cytokinins. Moreover, the previous study findings suggest that the LOG gene be expressed in a limited region of shoot apical meristems, that the number of rice grains be significantly decreased in a strain, wherein the LOG gene has been destroyed, and that there be a correlation between the content of cytokinins in such shoot apical meristems at the floral differentiation stage and the number of grains. Accordingly, it can be expected that the number of grains is increased in a rice transformed such that the LOG gene can be specifically expressed in shoot apical meristems, for example.

Furthermore, the expression level of the LOG gene in a plant body is locally or systemically regulated (promoted or suppressed) with a promoter such as a LOG promoter, a cytokinin oxidase 2 (OsCKX2) promoter, or a senescence-associated gene (SAG) promoter, so that the amount of active cytokinins in the plant can be regulated. As a result, it becomes possible to regulate various types of plant growth and physiological actions, with which cytokinins are associated, such as the number of grains, formation and extension of lateral buds (axillary buds), aging, dormancy, fruit abscission, cell cycle, photosynthetic amount, or transpiration.

(4) Production of Enzyme Proteins

A protein encoded by the aforementioned LOG gene can be obtained by transforming a host with a recombinant vector into which the gene has been introduced, so as to obtain a transformant, culturing the transformant, and then collecting the protein form the culture. The term "culture" is used herein to mean any one of a culture supernatant, a cultured cell or cultured cell mass, and a crushed product of the cultured cell or cell mass.

Herein, any type of recombinant vector may be used, as long as it is able to replicate in a host. Examples of such a recombinant vector include a plasmid DNA and a phage DNA. Examples of such plasmid DNA include a plasmid derived from *E. coli* (e.g. pBR322, pBR325, pUC118, pUC119, pUC18, pUC19, pBluescript, etc.), a plasmid derived from *Bacillus subtilis* (e.g. pUB110, pTP5, etc.), and a plasmid derived from yeast (e.g. YEp13, Yep24, YCp50, etc.). Examples of phage DNA include the λ phage (e.g. Charon4A, Charon21A, EMBL3, EMBL4, λgt10, λgt11, λZAP, etc.). Further, animal virus vectors such as a retrovirus and a vaccinia virus and insect virus vectors such as a baculovirus can also be used.

The aforementioned vector may comprise a replication origin, a promoter, and a selective marker. As necessary, the vector may further comprise an enhancer, a terminator, a ribosome-binding site, a polyadenylation signal, etc.

As a replication origin, those derived from ColE1, an R factor or an F factor can be used in vectors for *E. coli*, for example. Those derived from 2 μm DNA or ARS1 can be used in vectors for yeast, for example. Those derived from SV40 or adenovirus can be used in vectors for animals, for example.

As a promoter, a trp promoter, a lac promoter, a PL promoter, a PR promoter, cspA promoter, etc. can be used in vectors for *E. coli*. A gal1 promoter, a PH05 promoter, a PGK promoter, a GAP promoter, an ADH promoter, an AOX1 promoter, etc. can be used in vectors for yeast. An SRα promoter, an SV40 promoter, an LTR promoter, a CMV promoter, etc. can be used in vectors for animal cells.

As a selective marker, a kanamycin resistance gene, an ampicillin resistance gene, a tetracycline resistance gene, etc. can be used in vectors for *E. coli*. Leu2, Trp1, or Ura3 genes, etc. can be used in vectors for yeast. A neomycin resistance gene, a thymidine kinase gene, a dihydrofolate reductase gene, etc. can be used in vectors for animal cells.

As a host, either a prokaryote or an eukaryote can be used. Examples of such a prokaryote include bacteria belonging to genus *Escherichia* such as *E. coli*, genus *Bacillus* such as *Bacillus subtilis*, and genus *Pseudomonas* such as *Pseudomonas putida*. On the other hand, examples of such an eukaryote include: yeast such as *Saccharomyces cerevisiae* or *Schizosaccharomyces pombe*; animal cells such as COS cells, CHO cells, Vero, or C123 cells; and insect cells such as Sf9 or SF12.

The aforementioned transformed cells are cultured by a method generally used in the culture of a host. As a medium for culturing a transformant obtained from a microorganism host such as *E. coli* or yeast, either a natural or synthetic medium may be used, as long as it contains carbon sources, nitrogen sources, and inorganic salts assimilable by the microorganism and is capable of efficiently culturing the transgenic plant. Examples of carbon sources include: carbohydrates such as glucose, fructose, sucrose, and starch; organic acids such as acetic acid and propionic acid; and alcohols such as ethanol and propanol. Examples of nitrogen sources include: ammonia; ammonium salts of inorganic or organic acids such as ammonium chloride, ammonium sulfate, ammonium acetate, and ammonium phosphate; other nitrogen-containing compounds; peptone; meat extract; and corn steep liquor. Examples of inorganic substances include: monopotassium phosphate, dipotassium phosphate, magnesium phosphate, magnesium sulfate, sodium chloride, ferrous sulfate, manganese sulfate, copper sulfate, and calcium carbonate. Usually, culture is carried out under aerobic conditions such as shaking culture or aeration agitation culture at a temperature between 25° C. and 35° C. for 12 to 48 hours. The pH is adjusted with an inorganic or organic acid, an alkali solution, or the like. During the culture, an antibiotic such as ampicillin or tetracycline may be added to the medium, as necessary.

If the target protein is produced in the relevant cell mass or cell after the culture, the protein of interest is extracted by disrupting the cultured microorganism or cell via ultrasonication, repeated freeze-thaw cycles, or processing with a homogenizer. If the target protein is secreted outside of the microorganism or cell, the culture fluid may be used in that state or subjected to centrifugation or another procedure to remove the microorganism or cell. Thereafter, conventional biochemical techniques for isolating/purifying a protein such as ammonium sulfate precipitation, gel chromatography, ion exchange chromatography, or affinity chromatography, are employed independently or in an appropriate combination to isolate and purify the protein of the present invention from the above culture product.

(5) Synthesis of Active Cytokinins

In the present invention, when a transformant obtained by transformation with a recombinant vector comprising the aforementioned LOG gene is cultured in a medium, nucleotide cytokinins are added as substrates to the medium, so as to synthesize active cytokinins in the culture. The nucleotide cytokinins used as substrates are as described above.

In addition, the use of a transformant with higher proliferative ability provides a higher production amount of active cytokinins per unit culture solution and per unit time. Thus, it is preferable that a transformant be first activated by pre-culture, and that it be then inoculated into a medium for main culture that is used in production of active cytokinins, so that it be cultured.

The content of a substrate in the medium for pre-culture and in the medium for main culture is approximately 0.1% to 1.0% in terms of a solid content in the medium. The amount of a transformant used in the medium may be approximately 1 to 100 mg per L of medium, when a cell mass is inoculated therein, for example. The amount of a transformant may be increased or decreased, as appropriate, depending on the content of a substrate.

Such a substrate may be added at one time at the beginning of culture, or it may also be added continuously or intermittently during the culture. In addition, the generated active cytokinins may be collected at one time after completion of the culture, or it may also be collected continuously or intermittently during the culture.

The culture is terminated when the amount of desired active cytokinins generated in the culture solution reaches the maximum. After completion of the culture, the active cytokinins contained in the culture solution are purified therefrom according to a common method. Purification may be carried out by publicly known means generally used in the present technical field, such as filtration, centrifugation, ion exchange or adsorption chromatography, or solvent extraction. Such operations may be appropriately combined, as necessary.

BEST MODE FOR CARRYING OUT THE INVENTION

The present invention will be further specifically described in the following examples. However, these examples are not intended to limit the scope of the present invention.

Example 1

Abundant Expression of Recombinant LOG Protein in *E. Coli* and Purification Thereof The LOG gene (Accession number: AK071695 (nucleotide); BAD52880 (protein); Tigr locus: LOC_Os01g40630; RAP locus: Os01g0588900) had been estimated to encode a protein consisting of 242 amino acids, and it had been estimated to have a function as lysine decarboxylase on the NCBI database. However, a gene showing homology to the LOG gene is located extremely close to isopentenyltransferase (IPT) catalyzing an initial reaction of cytokinin biosynthesis on the fas locus of *Rhodococcus fasciens* or on the Ri plasmid of *Agrobacterium rhizogenes*. Thus, the following experiment was carried out to analyze the functions of a LOG protein.

First, the protein coding region of the LOG gene cDNA was inserted into pCOLD-I (TaKaRa), a His-tag protein expression vector used in *E. coli*, so as to construct a plasmid (pCOLD-LOG). Thereafter, *E. coli* BL21(DE3)[pG-Tf2] was transformed with this plasmid, and it was then dispersed on a Luria-Bertani agar medium containing 50 μg/ml ampicillin and 20 μg/ml chloramphenicol, so as to obtain a transformed *E. coli* colony. This *E. coli* colony was cultured in a Luria-Bertani medium containing 50 μg/ml ampicillin and 20 μg/ml chloramphenicol at 37° C. overnight. Thereafter, 30 ml of the culture solution obtained by the culture overnight was added to 270 ml of a modified M9 medium (M9 salt, IM sorbitol, 1% casamino acid, 2% sucrose, 1 mM MgSO$_4$, 0.1 mM CaCl$_2$, 10 µg/mL thiamine-HCl, and 2.5 mM betaine) that contained 100 µg/ml ampicillin, 20 µg/ml chloramphenicol and 1 ng/ml tetracycline, and the obtained mixture was then subjected to shaking culture at 37° C., until OD600 became approximately 0.5. The liquid medium was transferred into a 15° C. water bath, and it was then left at rest for 30 minutes. Thereafter, 1 M IPTG was added to the culture medium at a final concentration of 0.5 mM, and the obtained mixture was further subjected to shaking culture at 15° C. for 25 hours. Thereafter, E. coli cells were recovered by centrifugation.

Extraction of a protein from E. coli and purification of the LOG protein using a nickel NTA superflow resin were carried out by the following methods. First, an E. coli pellet was suspended in 6 ml of a Lysis buffer [50 mM NaHPO$_4$, 300 mM NaCl, 10 mM imidazole, 1 mM MgCl$_2$, 0.5 mM dithiothreitol (DTT), pH 8.0]. Thereafter, 60 µl of protease inhibitor cocktail (X100, Sigma) and 6 mg of lysozyme chloride were added to the suspension, and the obtained mixture was then left at rest on ice for 30 minutes. Thereafter, the E. coli cells were disintegrated with an ultrasonic disintegrator (TIETECH Co., Ltd.). Disintegration conditions consisted of the use of a microchip, 20 seconds×8 times, a duty cycle of 50%, and an output of 5. The disintegrated solution was centrifuged at 30,000 g at 4° C. for 50 minutes. The supernatant was passed through a column formed with a nickel NTA superflow resin (Qiagen) that had previously been equilibrated with a Lysis buffer (column volume: 1 ml). Thereafter, the column was washed twice with 20 ml of a washing buffer [50 mM NaHPO$_4$, 300 mM NaCl, 20 mM imidazole, 1 mM MgCl$_2$, 0.5 mM DTT, 15% (w/v) glycerol, pH 8.0], and a His-tag LOG protein was eluted with an elution buffer [50 mM NaHPO$_4$, 300 mM NaCl, 250 mM imidazole, 1 mM MgCl$_2$, 0.5 mM DTT, 15% (w/v) glycerol, pH 8.0]. The purity of the final purified sample was confirmed by SDS polyacrylamide electrophoresis (FIG. 1), and the sample was then used in the subsequent experiment.

Example 2

Detection of Enzyme Activity of Recombinant LOG Protein

3 µg of the recombinant LOG protein obtained in Example 1 was allowed to react with various types of cytokinins used as substrates. The following 8 types of cytokinin substrates were used: N$^6$-(delta-2-isopentenyl)adenine (iP), trans-zeatin (tZ), cis-zeatin (cZ), iP riboside (iPR), tZ riboside (tZR), cZ riboside (cZR), iPR 5'-monophosphate (iPRMP), and tZR 5'-monophosphate (tZRMP). As reaction conditions, 100 µl of a reaction solution containing 50 mM Tris-HCl, 1 mM MgCl$_2$, and a 50 µM substrate, pH7 was incubated at 30° C. for 2 hours. Thereafter, 10 µl of 20% acetic acid was added to the reaction solution to terminate the reaction, and the reaction solution was then centrifuged at 15,000 rpm at a room temperature for 20 minutes. Thereafter, 20 µl of a supernatant was analyzed by liquid chromatography using HPLC (Waters Alliance 2695/PDA detector 2996). As a column, Symmetry C18, 3.5 µm, 2.1×100 mm cartridge (Waters) was used. For elution, solvent C (100% acetonitrile) and solvent D (2% acetic acid) were used. Elution conditions and a solvent concentration gradient program are as shown in the following Table 1.

TABLE 1

| Time (min) | Flow rate (ml/min) | A (%) | B (%) | C (%) | D (%) | Curve |
|---|---|---|---|---|---|---|
|  | 0.25 | 0 | 0 | 1 | 99 |  |
| 1 | 0.25 | 0 | 0 | 1 | 99 | 6 |
| 3 | 0.25 | 0 | 0 | 7 | 93 | 6 |
| 9 | 0.25 | 0 | 0 | 10 | 90 | 6 |
| 25 | 0.25 | 0 | 0 | 40 | 60 | 6 |
| 26 | 0.25 | 0 | 0 | 60 | 40 | 6 |
| 32 | 0.25 | 0 | 0 | 60 | 40 | 6 |
| 33 | 0.25 | 0 | 0 | 1 | 99 | 6 |
| 40 | 0.25 | 0 | 0 | 1 | 99 | 6 |

The substrate and the reaction product were monitored based on the absorption at 270 nm. As a result of the analysis, it was found that when iP, tZ, cZ, iPR, tZR, or cZR was used as a substrate, no reactivity to the substrate was observed, but that when iPRMP or tZRMP was used as a substrate, each substrate was completely converted to iP or tZ. FIG. 2 shows the chromatogram of each substrate sample mixture and the chromatogram of a reaction product obtained when tZ, iPRMP, or tZRMP was used as a substrate. The results obtained when iP, cZ, iPR, tZR, or cZR was used as a substrate were the same as those in the case of tZ. Thus, such results were omitted.

Example 3

Reactivity of LOG Protein to Lysine

The LOG protein had previously been estimated to be lysine decarboxylase. Thus, the presence or absence of the reactivity of the LOG protein to lysine was examined. 3 µg of a recombinant LOG protein was incubated in 100 µl of a reaction solution consisting of 500 mM sodium acetate, pH 6.0, and 5 mM L-lysine, at 40° C. for 60 minutes. Thereafter, 34 µl of 20% trichloroacetate was added to the reaction solution, and the mixture was centrifuged at 10,000 g for 20 minutes. Thereafter, 100 µl of a supernatant was used for benzoylation. Specific operations are as described below. 100 µl of 2 N NaOH was added to 100 µl of the reaction solution, and 0.5 µl of benzoyl chloride was further added thereto. The obtained mixture was left at rest at a room temperature for 20 minutes. Thereafter, 200 µl of a saturated NaCl solution and 200 µl of diethylether were added to the reaction solution, and the obtained mixture was then stirred and centrifuged, followed by recovering a supernatant. The recovered supernatant was dried under a reduced pressure, and it was then dissolved in 100 µl of methanol, followed by the analysis by liquid chromatography using HPLC (Waters Alliance 2695/PDA detector 2996). As a column, Symmetry C18, 3.5 µm, 2.1×100 mm cartridge (Waters) was used. For elution, solvent A (Milli Q water) and solvent B (100% methanol) were used. Elution conditions and a solvent concentration gradient program are as shown in the following Table 2.

TABLE 2

| Time (min) | Flow rate (ml/min) | A (%) | B (%) | C (%) | D (%) | Curve |
|---|---|---|---|---|---|---|
|  | 0.25 | 70 | 30 | 0 | 0 |  |
| 15 | 0.25 | 50 | 50 | 0 | 0 | 6 |
| 30 | 0.25 | 50 | 50 | 0 | 0 | 6 |
| 37 | 0.25 | 35 | 65 | 0 | 0 | 6 |
| 40 | 0.25 | 20 | 80 | 0 | 0 | 6 |
| 42.5 | 0.25 | 20 | 80 | 0 | 0 | 6 |
| 45.5 | 0.25 | 0 | 100 | 0 | 0 | 6 |

TABLE 2-continued

| Time (min) | Flow rate (ml/min) | A (%) | B (%) | C (%) | D (%) | Curve |
|---|---|---|---|---|---|---|
| 48 | 0.25 | 0 | 100 | 0 | 0 | 6 |
| 50 | 0.25 | 70 | 30 | 0 | 0 | 6 |
| 54 | 0.25 | 70 | 30 | 0 | 0 | 6 |

Figure 3:
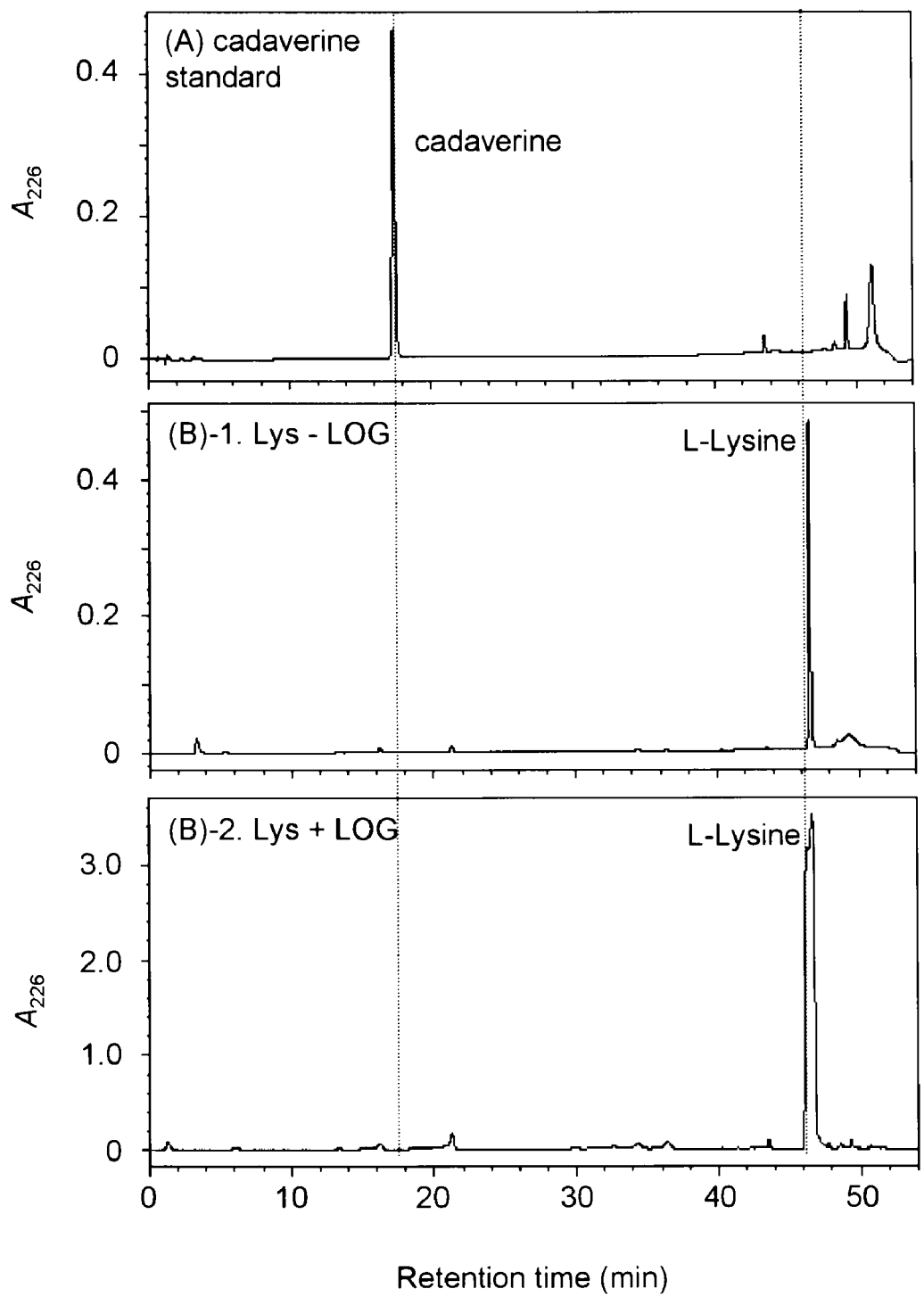
FIG. 3A shows a chromatogram of a cadaverine sample.
FIG. 3(B) shows a chromatogram of a reaction product obtained by allowing L-lysine used as a substrate to react with a purified LOG protein ((B)-1: only the substrate; (B)-2: the reaction product).

The substrate and the reaction product were monitored based on the absorption at 226 nm. A purified substance generated from lysine decarboxylase was estimated to be cadaverine. Thus, 1 nmol of a cadaverine sample was injected, separately, and the elution time of a reaction product was specified. As shown in FIG. 3, the LOG protein did not exhibit reactivity to lysine. Accordingly, it was determined that the LOG protein does not have a function as lysine decarboxylase, differing from estimation based on the database.

Example 4

Analysis Regarding Presence or Absence of Substrate Specificity to Nucleotide Cytokinin The reaction specificity of the LOG protein to a nucleotide cytokinin form was analyzed. At the same time, the presence or absence of the reactivity of the LOG protein to AMP was also analyzed. The following 7 types of substrates were used: iPRMP, tZRMP, dihydrozeatin riboside 5'-monophosphate (DZRMP), cZR 5'-monophosphate (cZRMP), iPR 5'-diphosphate (iPRDP), iPR 5'-triphosphate (iPRTP), and AMP. The reaction conditions are as follows. 0.02 μg of the LOG protein was used for a single reaction, and it was reacted with a 100 μM substrate in 200 μl of a reaction solution containing 50 mM Tris-HCl, 1 mM $MgCl_2$, 1 mM DTT, pH 6.5. Thereafter, 0 minute and 4 minutes after initiation of the reaction, 600 μl of cold acetone was added to the reaction solution to terminate the reaction. The reaction solution was left at rest at −80° C. for 30 minutes, and it was then centrifuged at 15,000 rpm for 20 minutes. Thereafter, a supernatant was dried using a centrifugal thickener. The resultant was dissolved in 100 μl of 2% acetic acid, and the reaction product was then detected and quantified under the same conditions as those for the liquid chromatography of Example 2. Only the injection amount was changed to 50 μl. In the case of iPRDP and iPRTP, the amount of a reaction solution was determined to be 100 μl, the mass of a protein used was determined to be 0.01 μg, and the reaction time was determined to be 2 minutes.

Figure 4:
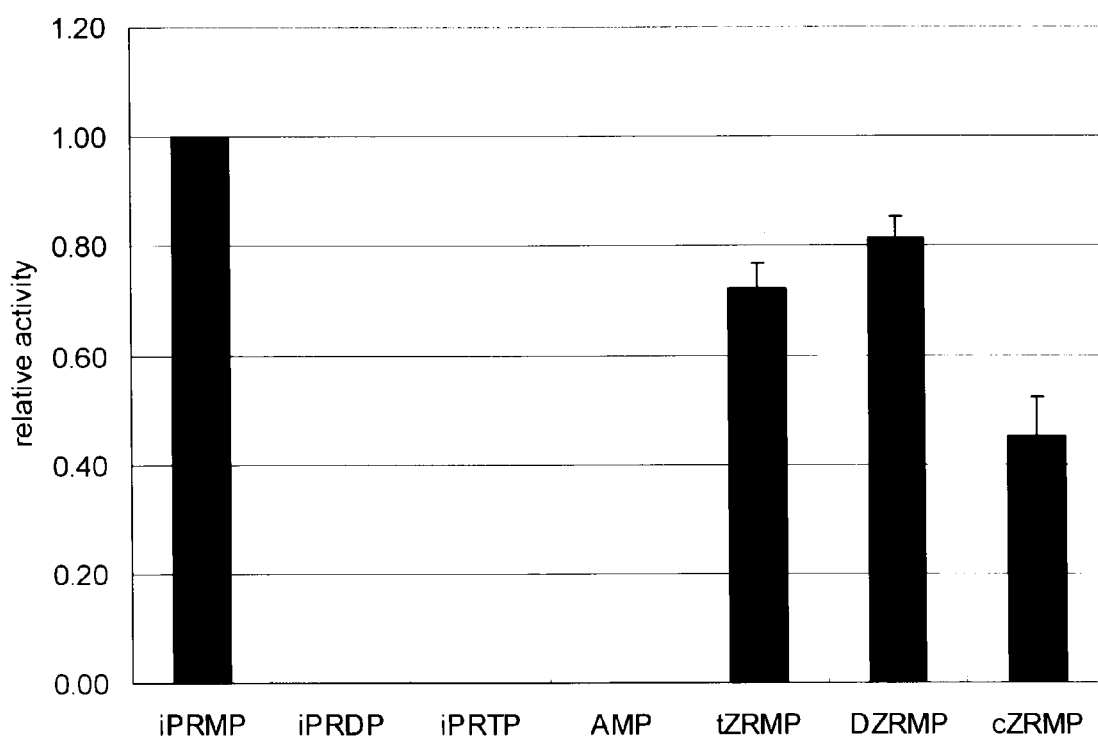
FIG. 4 shows the substrate specificity of a LOG protein. (Activity obtained when iPRMP was used as a substrate was defined as 1, and activity obtained by allowing each compound to react with the LOG protein under the same conditions was indicated as a relative value.)

From the results as shown in FIG. 4, it was revealed that the LOG protein uses as a substrate, cytokinin nucleoside 5'-monophosphate such as tZRMP, DZRMP or cZRMP, as well as iPRMP. However, the LOG protein showed no reactivity to AMP, iPRDP and iPRTP.

Figure 5:
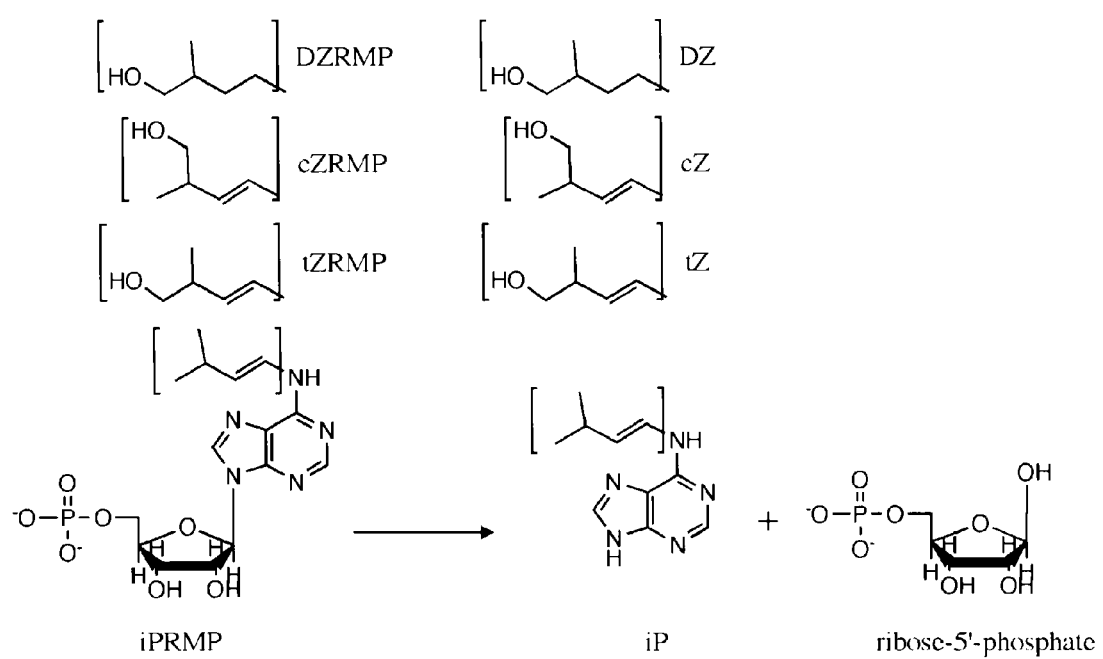
FIG. 5 is a synthesis reaction formula showing the synthesis of active cytokinins from nucleotide cytokinins, which is catalyzed by a LOG protein.

From these results, it was clarified that although the LOG protein had been estimated to have a function as lysine decarboxylase on database, in reality, it is an enzyme that catalyzes a completely novel reaction of removing ribose 5'-monophosphate from a nucleotide cytokinin and generating active cytokinin of a base form. The reaction catalyzed by the LOG protein is as shown in FIG. 5. From these results, it can be said that it is adequate that the trivial name of the LOG protein be cytokinin nucleoside 5'-monophosphate phosphoribohydrolase.

Example 5

Measurement of Km Value of LOG Protein to iPRMP and tZRMP

In order to obtain the Km value of the LOG protein to typical substrates iPRMP and tZRMP, the following experiment was carried out. 0.02 μg of LOG protein was used for a single reaction, and it was reacted with a substrate in a substrate concentration of each of 5, 8, 15, 30 and 100 μM in 200 μl of a reaction solution containing 50 mM Tris-HCl, 1 mM $MgCl_2$, 1 mM DTT, pH 6.5. Thereafter, 0 minute, 2 minutes and 4 minutes after initiation of the reaction, 600 μl of cold acetone was added to the reaction solution to terminate the reaction. The reaction solution was left at rest at −80° C. for 30 minutes, and it was then centrifuged at 15,000 rpm for 20 minutes. Thereafter, a supernatant was dried using a centrifugal thickener. The resultant was dissolved in 100 μl of 2% acetic acid, and a reaction product was then detected and quantified under the same conditions as those for the liquid chromatography of Example 2. Only the injection amount was changed to 50 μl. The aforementioned experiment was carried out three times, and the Km value was calculated. As a result, the Km value to iPRMP was found to be 11.7±1.4 μM, and the specific activity was found to be 5.6 μmol/min$^{-1}$/mg$^{-1}$ protein. The Km value to tZRMP was found to be 22.0±3.6 μM, and the specific activity was found to be 4.2 μmol/min$^{-1}$/mg$^{-1}$ protein.

Example 6

Isolation of cDNAs of *Arabidopsis thaliana* LOG Homolog Genes (AtLOGs)

Figure 6:
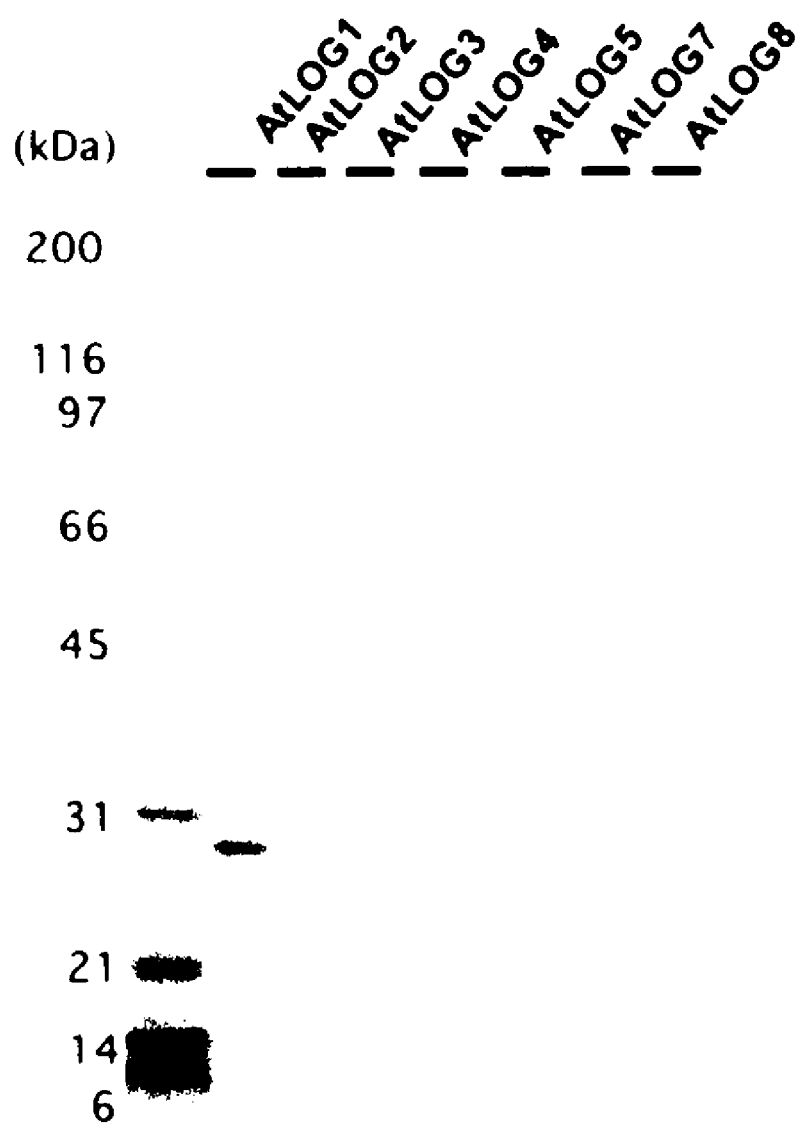
FIG. 6 shows the results obtained by performing SDS polyacrylamide electrophoresis on purified samples of AtLOG 1, 2, 3, 4, 5, 7 and 8 proteins (leftmost lane: a molecular weight marker; each lane: a band observed around a molecular weight of 31 kDa is each AtLOG protein-derived band).

Whether or not a cytokinin-activating enzyme having the same functions as those of the LOG protein exists not only in rice but also in *Arabidopsis thaliana* was examined. First, protein BLAST search was conducted through the NCBI database based on the amino acid sequence of the LOG protein, so that the homologous genes thereof were searched in *Arabidopsis thaliana*. As a result, 9 *Arabidopsis thaliana* genes, AtLOG 1-9 (*Arabidopsis thaliana* LOG 1-9; Table 3), which were predicted to encode proteins showing high homology to the LOG protein, were discovered. Whether or not these genes were transcribed as mRNA sequences in an *Arabidopsis thaliana* plant body, predicted in the TAIR database, were examined. That is, mRNA was extracted from an *Arabidopsis thaliana* plant body, and an RT-PCR reaction was carried out, using cDNA synthesized by a reverse transcription reaction as a template, and also using primers designed to amplify a putative protein coding region. As a result, with regard to AtLOG 1, 2, 3, 4, 5, 7 and 8, an amplified fragment having the same sequence as a cDNA sequence predicted in the TAIR database was successfully obtained. Such 7 gene products were predicted to have a function as a cytokinin-activating enzyme, as with a rice LOG protein. Thus, with regard to the cDNA sequences of such 7 genes, induction of protein expression in *E. coli* and purification thereof were carried out by the same method for the rice LOG cDNA. The purity of the final purified sample was confirmed by SDS polyacrylamide electrophoresis (FIG. 6), and the product was used in the subsequent experiment.

TABLE 3

Genes in *Arabidopsis thaliana* genome showing high homology to LOG protein

| Gene name | AGI Code | Putative amino acid length | Putative molecular weight (kDa) | Homology (%) to LOG |
|---|---|---|---|---|
| AtLOG1 | At2g28305 | 213 | 23.2 | 76.1 |
| AtLOG2 | At2g35990 | 213 | 25.3 | 70.6 |
| AtLOG3 | At2g37210 | 215 | 23.6 | 79.9 |
| AtLOG4 | At3g53450 | 215 | 23.5 | 81.0 |
| AtLOG5 | At4g35190 | 228 | 25.2 | 67.4 |
| AtLOG6 | At5g03270 | 229 | 25.0 | 67.6 |
| AtLOG7 | At5g06300 | 217 | 23.9 | 72.2 |
| AtLOG8 | At5g11950 | 216 | 23.8 | 65.6 |
| AtLOG9 | At5g26140 | 143 | 16.1 | 63.7 |

Example 7

Confirmation of LOG Enzyme Activity of *Arabidopsis thaliana* LOG Homolog Proteins (AtLOGs)

Figure 7:
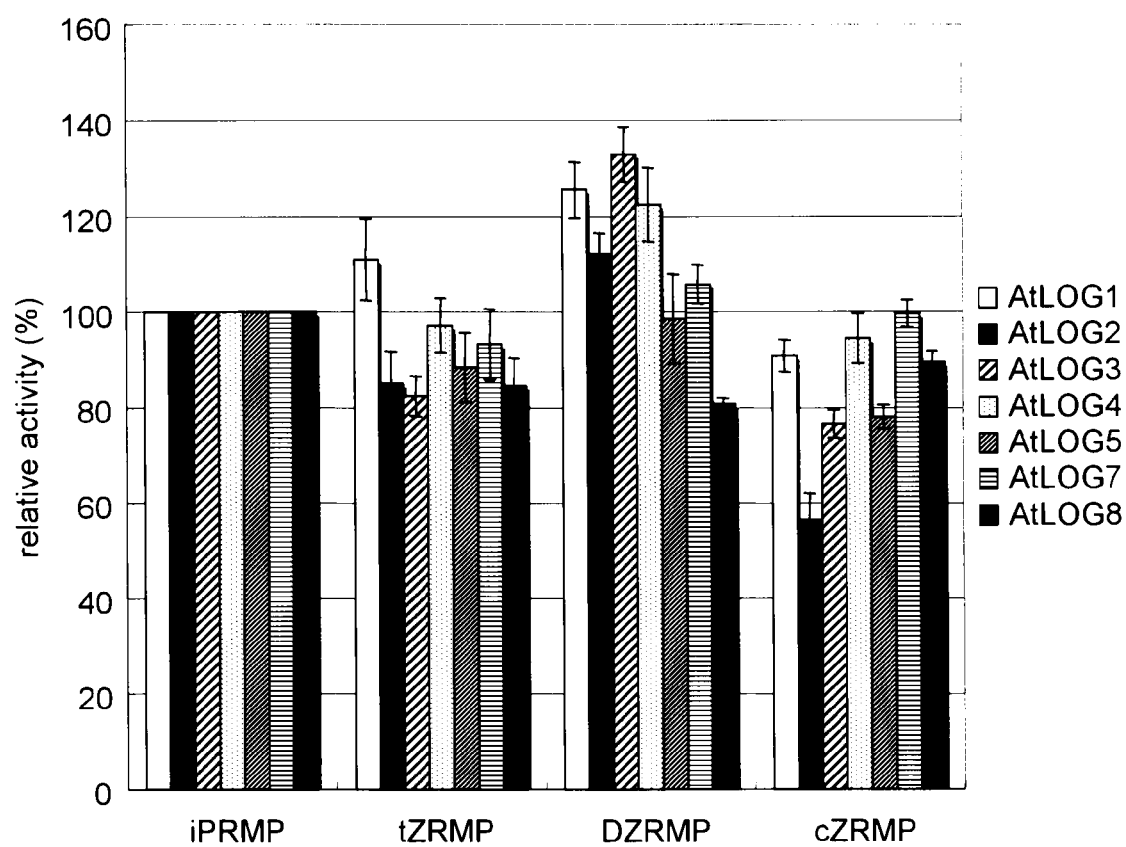
FIG. 7 shows the substrate specificity of each of AtLOG 1, 2, 3, 4, 5, 7 and 8 proteins. (Activity obtained when iPRMP was used as a substrate was defined as 100%, and activity obtained by allowing each compound to react with each of the aforementioned proteins under the same conditions was indicated as a relative value. The error bar indicates a standard deviation calculated based on the results obtained by performing the operation 3 times under the same conditions.)

The enzyme activity of each of the purified AtLOG proteins was evaluated under the same reaction conditions as those of Example 2. As a result, it became clear that the AtLOG proteins also have cytokinin nucleoside 5'-monophosphate such as iPRMP, tZRMP, DZRMP or cZRMP as a substrate, as in the case of the LOG protein (FIG. 7). Further, as with the LOG protein, such AtLOG proteins showed almost no reactivity to AMP, iPRDP and iPRTP. In addition, the enzyme property of each AtLOG protein to iPRMP was determined in the same manner as in Example 5 (Table 4). In Table 4, the $K_m$, $V_{max}$ and $K_{cat}$ values were calculated based on a reaction under the optimal pH condition of each AtLOG protein. The symbol "±" indicates a standard deviation calculated based on the results obtained by performing the operation 3 times under the same conditions.

TABLE 4

Enzyme properties of AtLOG 1, 2, 3, 4, 5, 7 and 8 proteins having iPRMP as substrate

| Enzyme | $K_m$ μM | $V_{max}$ μmol min$^{-1}$ mg$^{-1}$ protein | $k_{cat}$ min$^{-1}$ | $k_{cat}/K_m$ min$^{-1}$ M$^{-1}$ | Optimal pH |
|---|---|---|---|---|---|
| AtLOG1 | 16 ± 2 | 2.1 ± 0.1 | 54 ± 4 | 3.5 × 10$^6$ | 6.5 |
| AtLOG2 | 126 ± 16 | 6.1 ± 2.0 | 166 ± 55 | 1.3 × 10$^5$ | 6.5 |
| AtLOG3 | 14 ± 2 | 1.5 ± 0.0 | 37 ± 1 | 2.8 × 10$^6$ | 6.5 |
| AtLOG4 | 8.6 ± 0.6 | 4.4 ± 0.2 | 113 ± 6 | 1.3 × 10$^7$ | 6.5 |
| AtLOG5 | 11 ± 1 | 0.73 ± 0.03 | 20 ± 1 | 1.8 × 10$^6$ | 5.4 |
| AtLOG7 | 6.7 ± 0.8 | 3.8 ± 0.2 | 99 ± 6 | 1.5 × 10$^7$ | 6.5 |
| AtLOG8 | 17 ± 1 | 0.053 ± 0.009 | 1.4 ± 0.2 | 8.3 × 10$^4$ | 7.0 |

Example 8

Production of Transformant in which *Arabidopsis thaliana* LOG Homolog Genes (AtLOGs) have been Excessively Expressed The influence of excessive expression of cytokinin-activating enzyme genes AtLOGs in *Arabidopsis thaliana* upon the plant body was examined. With regard to AtLOG 4 and 7 out of the AtLOG 1, 2, 3, 4, 5, 7 and 8 genes, wherein the presence of enzyme activity of a transcription product has been confirmed, cDNA isolated in terms of enzyme activity was inserted into a site downstream of a tobacco mosaic virus 35S promoter of the plasmid pBI121 (Clontech) from which a GUS gene had been eliminated. The synthesized plasmid was introduced into *Agrobacterium tumefaciens*, and wild-type *Arabidopsis thaliana* was then infected with *Agrobacterium tumefaciens*, regarding which introduction of the plasmid had been confirmed by PCR. The collected seeds were inoculated into an MS medium containing 50 ng/ml kanamycin. Utilizing the fact that a kanamycin resistance gene (NPTII) exists in the T-DNA region of pBI121, individuals exhibiting resistance to kanamycin were selected. For each of AtLOG 4 and AtLOG 7, twenty-six kanamycin resistance lineages that had been succeeded in gene introduction (hereinafter referred to as 35S::AtLOG4 and 35S::AtLOG7) were selected. The selected 35S::AtLOG 4 and 35S::LOG 7 transformants of T1 generation exhibited phenotypes that were similar to each other.

Figure 8:
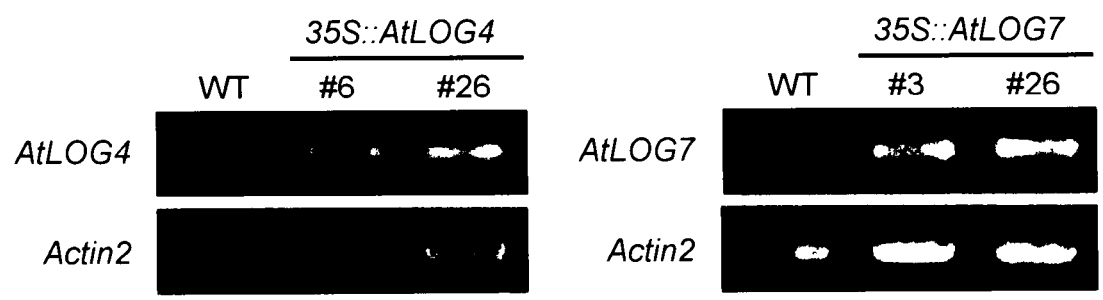
FIG. 8 shows the semiquantitative RT-PCR analysis results of AtLOG4 and 7 genes in 35S::AtLOG4 and 35S::AtLOG7 transformants.

The mRNA of each of the 35S::At LOG 4 (lineage #6 and #26) and 35S::At LOG 7 (lineage #3 and #26) transformants of T1 generation extracted from rosette leaves was subjected to a reverse transcription reaction to synthesize cDNA. Using the cDNA as a template, and also using primers for amplification of the AtLOG 4 and 7 genes and an Actin2 gene, semi-quantitative RT-PCR analysis was carried out. cDNA (WT) derived from wild-type rosette leaves was used as a control. In the RT-PCR reaction, 25 cycles were applied to AtLOG 4, whereas 35 cycles were applied to Actin2 and AtLOG 7. As a result, in the plant bodies of each 2 lineages, excessive expression of the AtLOG 4 and AtLOG 7 genes was confirmed (FIG. 8).

Example 9

Figure 9:
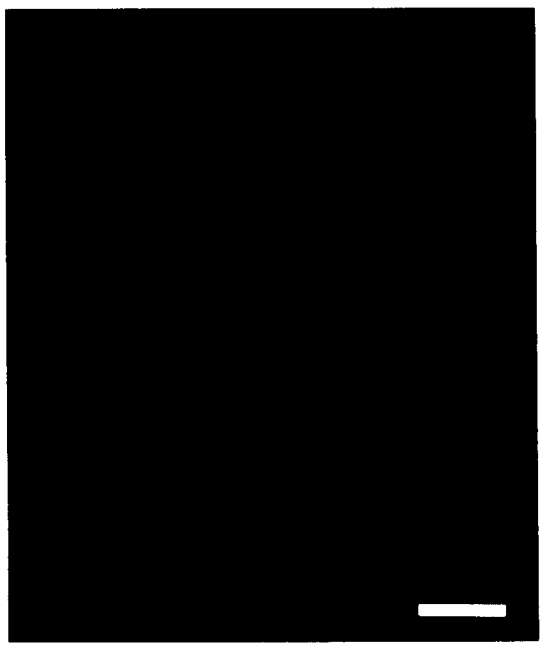
FIG. 9 shows the abnormality of rosette leaves observed in the 35S::AtLOG7 transformant. The rosette leaves of a wild-type plant and a 35S::AtLOG7 transformant (lineage #6; T1 generation) obtained at 1.5 months after germination were observed under a stereoscopic microscope (scale: 1 mm).
Figure 9:
Figure 10:
FIG. 10 shows the abnormality of rosette leaves observed in the 35S::AtLOG4 transformant. The rosette leaves of a wild-type plant and a 35S::AtLOG4 transformant (lineage #26; T1 generation) obtained at 1.5 months after germination were decolorized and fixed with 70% ethanol, and were then observed under a stereoscopic microscope (scale: left 0.5 cm; right 2 mm).
Figure 11:
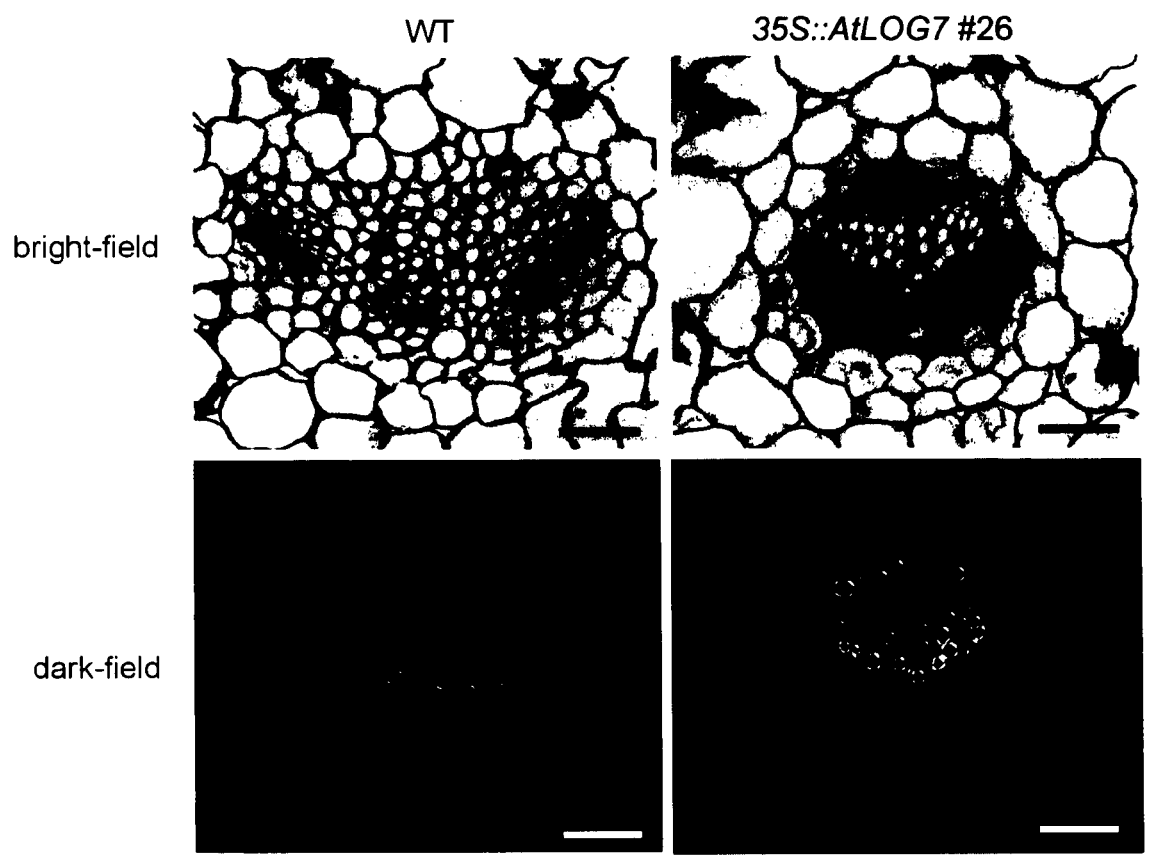
FIG. 11 shows the malformation of the vascular bundle of a 35S::AtLOG7 transformant. The rosette leaves of a wild-type plant and a 35S::AtLOG7 transformant (lineage #26; T2 generation) obtained at 1 month after germination were decolorized and fixed with 70% ethanol, and were then fixed with a Technovit resin, followed by cutting with a microtome, so as to produce a horizontal section. The horizontal section was stained with toluidine blue, and it was then observed under an optical microscope. A portion that became white under dark field conditions indicates a vessel (scale: 50 μm).
Figure 12:
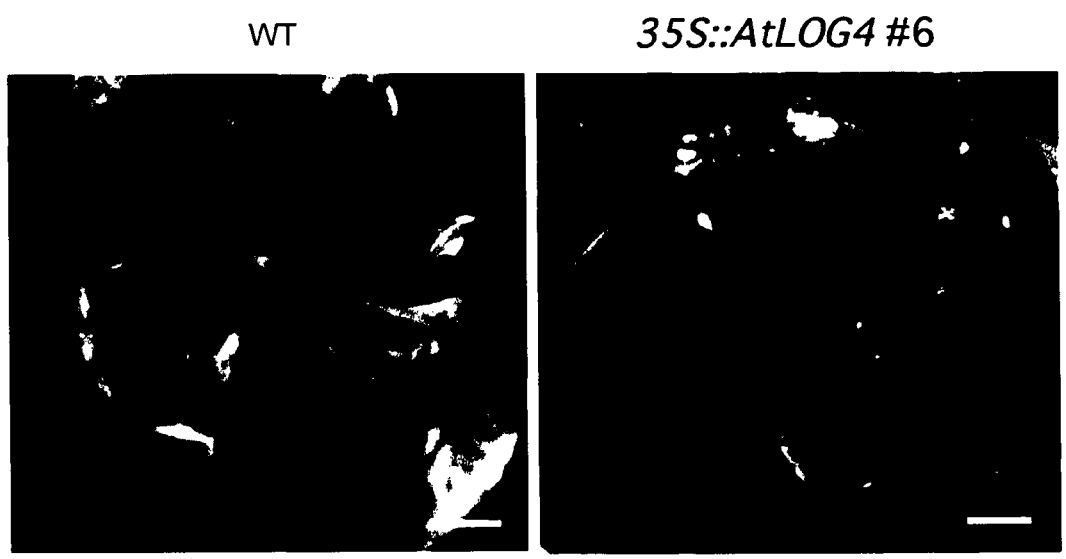
FIG. 12 shows the delay of the aging of leaves of a 35S::AtLOG4 transformant. The rosette leaves of a wild-type plant and a 35S::AtLOG4 transformant (lineage #6; T1 generation) obtained at 70 days after germination were used (scale: 1 cm).

Phenotypes of Transformants in which *Arabidopsis thaliana* LOG Homolog Genes (AtLOGs) have been Excessively Expressed It was confirmed that the 35S::AtLOG 4 and 35S::LOG 7 transformants exhibited phenotypes that were similar to each other, and that such phenotypes were inherited from T1 generation to T2 generation. When compared with wild-type plants, the 35S::AtLOG 4 and 35S::LOG 7 transformants did not particularly show morphological abnormality until approximately 1 week after germination. However, from approximately 2 weeks after germination, at which many rosette leaves were formed and grew, significant morphological abnormality was observed. The 35S::AtLOG 4 and 35S::LOG 7 transformants formed deep green rosette leaves along the veins (FIG. 9). When the leaves were fixed and decolorized with 70% ethanol, it was observed that the vascular bundles on the leaves were significantly developed when compared with wild-type plants (FIG. 10). Thus, the horizontal section of such leaf was observed. As a result, significant morphological abnormality such as heterotopic formation of vessel was observed in the vascular bundle system (FIG. 11). Moreover, a phenomenon whereby the aging of leaves was delayed was also observed (FIG. 12).

Figure 13:
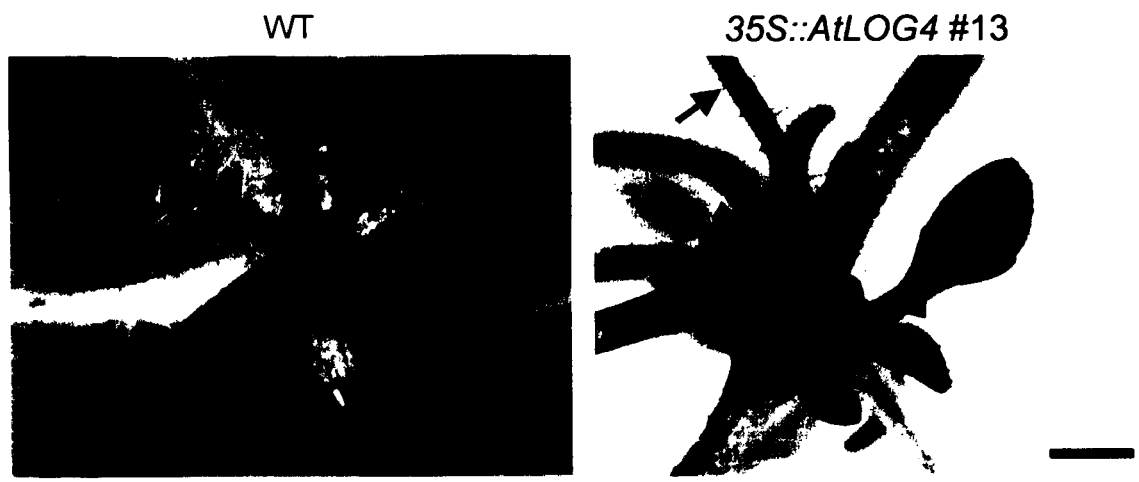
FIG. 13 shows promotion of the lateral bud formation of a 35S::AtLOG4 transformant. The aerial parts of a wild-type plant and a 35S::AtLOG4 transformant (lineage #13; T2 generation) obtained at 3 weeks after germination were observed under a stereoscopic microscope (arrow: elongated scapes; triangle: grown lateral buds; scale: 1 mm).
Figure 14:
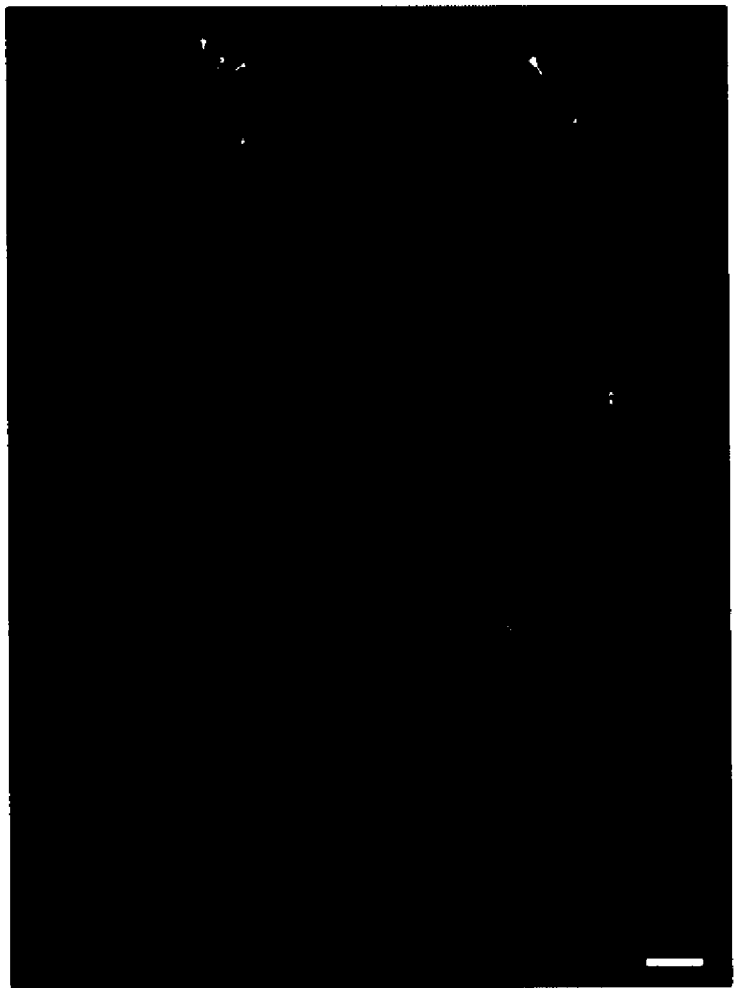
FIG. 14 shows the abnormality of inflorescence of a 35S::AtLOG7 transformant. The inflorescences of a wild-type plant and a 35S::AtLOG7 transformant (lineage #6; T1 generation) obtained at 3 weeks after germination were observed (scale: 1 cm).
Figure 15:
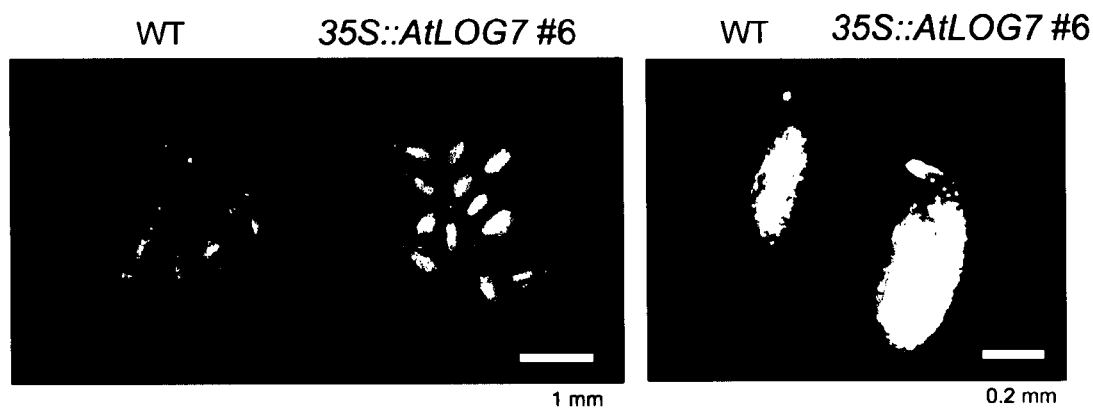
FIG. 15 shows an increase in the seed size of a 35S::AtLOG4 transformant. The seeds of a wild-type plant and a 35S::AtLOG4 transformant (lineage #26; T2 generation) were observed under a stereoscopic microscope (scale: left 1 cm; right 0.2 mm).
Figure 16:
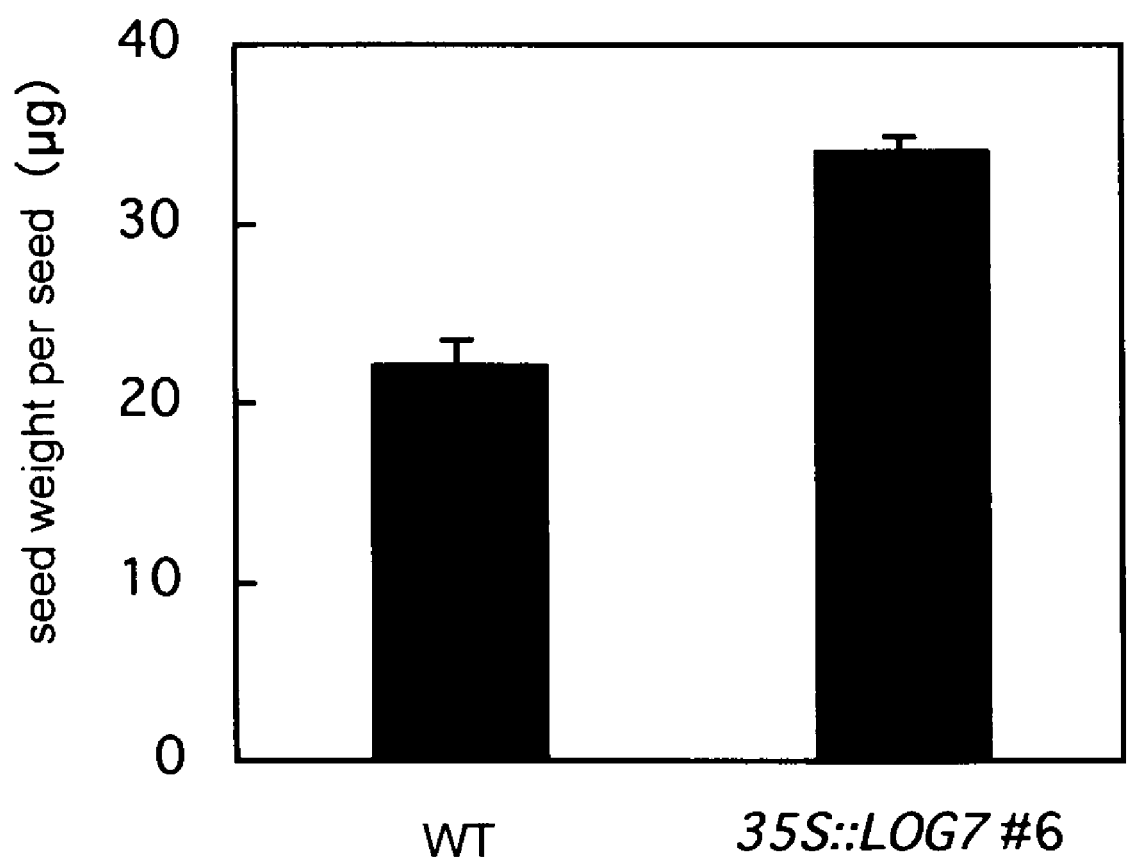
FIG. 16 shows an increase in the seed weight of a 35S::AtLOG7 transformant. The weight of 100 seeds from each of a wild-type plant and a 35S::AtLOG7 transformant (lineage: #6; T2 generation) was measured, and a weight per grain was then calculated. The error bar indicates a standard deviation calculated based on the results obtained from 3 different types of seed pools.

In the case of wild-type plants, after a scape had extended, lateral buds were not developed for a while. However, in the case of the 35S::AtLOG 4 and 35S::LOG 7 transformants, a plurality of lateral buds were developed and leaves were also developed immediately after extension of a scape (FIG. 13). Furthermore, *Arabidopsis thaliana* generally exhibits the form of a raceme. However, in the case of the 35S::AtLOG 4 and 35S::LOG 7 transformants, the axis of inflorescence did not become a straight line, but exhibited a form like cincinnus (FIG. 14). Further, the size and weight of a seed contained in a case of such transformant was compared with those of a wild-type plant. As a result, it was confirmed that the size and weight of such seed of the transformant became significantly larger than those of the wild-type plant (FIGS. 15 and 16).

All publications, patents and patent applications cited herein are incorporated herein by reference in their entirety.

INDUSTRIAL APPLICABILITY

According to the present invention, it has newly been clarified that a rice gene, which had previously been considered as a gene encoding a lysine decarboxylase protein, has had a function to catalyze reactions that synthesize active cytokinins from nucleotide cytokinins (a cytokinin activation reaction) in a biosynthetic pathway of cytokinins. Accordingly, use of the present gene enables direct regulation of the amount of active cytokinins (a base form), which has previously been realized only by modification of a cytokinin decomposition reaction. Moreover, in a plant body wherein the present gene has been excessively expressed, changes in the character of the plant, such as an increase in the number of scapes, formation of large seeds, formation of thick veins, or a change in inflorescence, are observed. Thus, it can be expected that the use of the present gene brings on the improvement of commercial values of crops, such as an increase in the yield of crops or diversification of the characters of cut flowers or foliage plants.

The invention claimed is:

1. A method for producing a transformed plant, the method comprising
   introducing an isolated nucleic acid or recombinant vector comprising said isolated nucleic acid into a plant cell such that the amount of active cytokinin synthesized from nucleotide cytokinin is increased in the plant cell, and
   regenerating a plant body from the plant cell,
   wherein the isolated nucleic acid is:
   (a) an isolated nucleic acid consisting of SEQ ID NO:13;
   (b) an isolated nucleic acid consisting of a sequence which hybridizes under stringent conditions to SEQ ID NO:13 and encodes a protein having activity of catalyzing reactions that synthesize active cytokinin from nucleotide cytokinin, wherein the stringent conditions comprise washing in 15 mM to 600 mM sodium salt at 50° C. to 70° C.;
   (c) an isolated nucleic acid encoding a protein consisting of the amino acid sequence of SEQ ID NO:14; or
   (d) an isolated nucleic acid encoding a protein which consists of an amino acid sequence having 72.2% or higher homology to the amino acid sequence of SEQ ID NO:14 and that has activity of catalyzing reactions that synthesize active cytokinin from nucleotide cytokinin.

2. A method for regulating the amount of active cytokinin in a plant, the method comprising
   introducing an isolated nucleic acid in a plant operably linked to a promoter to control the expression level of the isolated nucleic acid in the plant such that the amount of active cytokinin synthesized from nucleotide cytokinin is increased in the plant cell,
   wherein the isolated nucleic acid is:
   (a) an isolated nucleic acid consisting of SEQ ID NO:13;
   (b) an isolated nucleic acid consisting of a sequence which hybridizes under stringent conditions to SEQ ID NO:13 and encodes a protein having activity of catalyzing reactions that synthesize active cytokinin from nucleotide cytokinin, wherein the stringent conditions comprise washing in 15 mM to 600 mM sodium salt at 50° C. to 70° C.;
   (c) an isolated nucleic acid encoding a protein consisting of the amino acid sequence of SEQ ID NO:14; or
   (d) an isolated nucleic acid encoding a protein which consists of an amino acid sequence having 72.2% or higher homology to the amino acid sequence NO:14 and that has activity of catalyzing reactions that synthesize active cytokinin from nucleotide cytokinin.

3. A method for producing active cytokinin from nucleotide cytokinin, the method comprising
   culturing a cell transformed with an isolated nucleic acid in a medium to which nucleotide cytokinin has been added as a substrate, and collecting active cytokinin from the culture,
   wherein the isolated nucleic acid is:
   (a) an isolated nucleic acid consisting of SEQ ID NO:13;
   (b) an isolated nucleic acid consisting of a sequence which hybridizes under stringent conditions to SEQ ID NO:13 and encodes a protein having activity of catalyzing reactions that synthesize active cytokinin from nucleotide cytokinin, wherein the stringent conditions comprise washing in 15 mM to 600 mM sodium salt at 50° C. to 70° C.;
   (c) an isolated nucleic acid encoding a protein consisting of the amino acid sequence of SEQ ID NO:14; or
   (d) an isolated nucleic acid encoding a protein which consists of an amino acid sequence having 72.2% or higher homology to the amino acid sequence of SEQ ID NO:14 and that has activity of catalyzing reactions that synthesize active cytokinin from nucleotide cytokinin.

4. A method for changing the character of a plant, the method comprising
   introducing an isolated nucleic acid operably linked to a promoter such that the isolated nucleic acid is overexpressed in the plant body such that the amount of active cytokinin synthesized from nucleotide cytokinin is increased in the plant cell, wherein the isolated nucleic acid is:
   (a) an isolated nucleic acid consisting of SEQ ID NO:13;
   (b) an isolated nucleic acid consisting of a sequence which hybridizes under stringent conditions to SEQ ID NO:13 and encodes a protein having activity of catalyzing reactions that synthesize active cytokinin from nucleotide cytokinin, wherein the stringent conditions comprise washing in 15 mM to 600 mM sodium salt at 50° C. to 70° C.;

(c) an isolated nucleic acid encoding a protein consisting of the amino acid sequence of SEQ ID NO:14; or (d) an isolated nucleic acid encoding a protein which consists of an amino acid sequence having 72.2% or higher homology to the amino acid sequence of SEQ ID NO:14 and that has activity of catalyzing reactions that synthesize active cytokinin from nucleotide cytokinin.

5. The method according to claim 4, wherein a change in the character of a plant involves an increase in the number of scapes, formation of large seeds, formation of thick veins, or a change in inflorescence.

6. The method according to claim 1, wherein the isolated nucleic acid is (a).

7. The method according to claim 1, wherein the isolated nucleic acid is (c).

8. The method according to claim 2, wherein the isolated nucleic acid is (a).

9. The method according to claim 2, wherein the isolated nucleic acid is (c).

10. The method according to claim 3, wherein the isolated nucleic acid is (a).

11. The method according to claim 3, wherein the isolated nucleic acid is (c).

12. The method according to claim 4, wherein the isolated nucleic acid is (a).

13. The method according to claim 4, wherein the isolated nucleic acid is (c).

* * * * *

SEQUENCE LISTING

```
<160> NUMBER OF SEQ ID NOS: 16

<210> SEQ ID NO 1
<211> LENGTH: 729
<212> TYPE: DNA
<213> ORGANISM: Oryza sativa
<220> FEATURE:
<221> NAME/KEY: CDS
<222> LOCATION: (1)..(729)

<400> SEQUENCE: 1 atg gca atg gag gct gcg gcg gag agg agc gcc gga gca ggg gcg gcg      48
Met Ala Met Glu Ala Ala Ala Glu Arg Ser Ala Gly Ala Gly Ala Ala
1               5                   10                  15 gcg acg gcg gcg ccg gag agc ggt ggc ggt ggt gca ggg gag agg cgg      96
Ala Thr Ala Ala Pro Glu Ser Gly Gly Gly Gly Ala Gly Glu Arg Arg
                20                  25                  30 tcg cgg ttc agg cgg atc tgc gtg tac tgc ggc agc gcc aag ggg agg     144
Ser Arg Phe Arg Arg Ile Cys Val Tyr Cys Gly Ser Ala Lys Gly Arg
            35                  40                  45 aag gcc agc tac cag gac gcc gcc gtc gag ctc ggc aag gaa ctg gtc     192
Lys Ala Ser Tyr Gln Asp Ala Ala Val Glu Leu Gly Lys Glu Leu Val
        50                  55                  60 gag agg ggc ata gac ctg gtc tac ggc ggt ggc tcc atc ggc ctc atg     240
Glu Arg Gly Ile Asp Leu Val Tyr Gly Gly Gly Ser Ile Gly Leu Met
65                  70                  75                  80 ggc ctc gtc tcc cac gct gtt cac gac ggt ggt cgc cat gtc att ggg     288
Gly Leu Val Ser His Ala Val His Asp Gly Gly Arg His Val Ile Gly
                85                  90                  95 gtc atc ccg aaa tcc ttg atg ccc aga gag gtc act ggt gag cct gtt     336
Val Ile Pro Lys Ser Leu Met Pro Arg Glu Val Thr Gly Glu Pro Val
            100                 105                 110 ggt gaa gtt aga gcg gtc tct ggc atg cac gag agg aag gct gaa atg     384
Gly Glu Val Arg Ala Val Ser Gly Met His Glu Arg Lys Ala Glu Met
        115                 120                 125 gcc cgg ttt gct gat gcg ttc att gca ctg cct ggc ggc tac ggg act     432
Ala Arg Phe Ala Asp Ala Phe Ile Ala Leu Pro Gly Gly Tyr Gly Thr
    130                 135                 140 ctt gag gag ttg ctt gag gtc atc acc tgg gcc caa cta gga atc cac     480
Leu Glu Glu Leu Leu Glu Val Ile Thr Trp Ala Gln Leu Gly Ile His
145                 150                 155                 160
```

```
aag aag ccg gtt ggc ctt ctg aat gtc gac ggg ttt tat gat cct ttt      528
Lys Lys Pro Val Gly Leu Leu Asn Val Asp Gly Phe Tyr Asp Pro Phe
            165                 170                 175 cta tcc ttc att gac atg gct gtc agc gaa gga ttc ata gcg gag gat      576
Leu Ser Phe Ile Asp Met Ala Val Ser Glu Gly Phe Ile Ala Glu Asp
            180                 185                 190 gcg cgg cgc att atc atc tcg gct cca act gcc agg gag cta gtt ctg      624
Ala Arg Arg Ile Ile Ile Ser Ala Pro Thr Ala Arg Glu Leu Val Leu
            195                 200                 205 aag ctt gag gag tat gtt ccc gag tac gag gtc ggc ttg gtt tgg gac      672
Lys Leu Glu Glu Tyr Val Pro Glu Tyr Glu Val Gly Leu Val Trp Asp
    210                 215                 220 gat cag atg ccg cac agc ttc gcg cct gac ctc gag acc agg atc acc      720
Asp Gln Met Pro His Ser Phe Ala Pro Asp Leu Glu Thr Arg Ile Thr
225                 230                 235                 240 tca tcc tga                                                          729
Ser Ser
```

<210> SEQ ID NO 2
<211> LENGTH: 242
<212> TYPE: PRT
<213> ORGANISM: Oryza sativa

<400> SEQUENCE: 2

```
Met Ala Met Glu Ala Ala Glu Arg Ser Ala Gly Ala Gly Ala Ala
1               5                   10                  15

Ala Thr Ala Ala Pro Glu Ser Gly Gly Gly Ala Gly Glu Arg Arg
                20                  25                  30

Ser Arg Phe Arg Arg Ile Cys Val Tyr Cys Gly Ser Ala Lys Gly Arg
            35                  40                  45

Lys Ala Ser Tyr Gln Asp Ala Ala Val Glu Leu Gly Lys Glu Leu Val
    50                  55                  60

Glu Arg Gly Ile Asp Leu Val Tyr Gly Gly Ser Ile Gly Leu Met
65                  70                  75                  80

Gly Leu Val Ser His Ala Val His Asp Gly Arg His Val Ile Gly
                85                  90                  95

Val Ile Pro Lys Ser Leu Met Pro Arg Glu Val Thr Gly Glu Pro Val
                100                 105                 110

Gly Glu Val Arg Ala Val Ser Gly Met His Glu Arg Lys Ala Glu Met
            115                 120                 125

Ala Arg Phe Ala Asp Ala Phe Ile Ala Leu Pro Gly Gly Tyr Gly Thr
            130                 135                 140

Leu Glu Glu Leu Leu Glu Val Ile Thr Trp Ala Gln Leu Gly Ile His
145                 150                 155                 160

Lys Lys Pro Val Gly Leu Leu Asn Val Asp Gly Phe Tyr Asp Pro Phe
                165                 170                 175

Leu Ser Phe Ile Asp Met Ala Val Ser Glu Gly Phe Ile Ala Glu Asp
                180                 185                 190

Ala Arg Arg Ile Ile Ile Ser Ala Pro Thr Ala Arg Glu Leu Val Leu
            195                 200                 205

Lys Leu Glu Glu Tyr Val Pro Glu Tyr Glu Val Gly Leu Val Trp Asp
    210                 215                 220

Asp Gln Met Pro His Ser Phe Ala Pro Asp Leu Glu Thr Arg Ile Thr
225                 230                 235                 240

Ser Ser
```

<210> SEQ ID NO 3
<211> LENGTH: 642
<212> TYPE: DNA
<213> ORGANISM: Arabidopsis sp.
<220> FEATURE:
<221> NAME/KEY: CDS
<222> LOCATION: (1)..(642)

<400> SEQUENCE: 3

```
atg gag ata gaa tca aag ttc aag aga ata tgt gtg ttt tgt gga agt        48
Met Glu Ile Glu Ser Lys Phe Lys Arg Ile Cys Val Phe Cys Gly Ser
1               5                   10                  15 agt gct ggt aat aaa gtc agt tac aaa gat gct gct atc gaa ctc gga        96
Ser Ala Gly Asn Lys Val Ser Tyr Lys Asp Ala Ala Ile Glu Leu Gly
            20                  25                  30 acc gaa ctg gta tcg aga aat atc gat ctt gtc tat ggt gga ggg agc       144
Thr Glu Leu Val Ser Arg Asn Ile Asp Leu Val Tyr Gly Gly Gly Ser
        35                  40                  45 att ggt tta atg ggt ttg att tct caa gct gtt ttc aat gga ggt cgc       192
Ile Gly Leu Met Gly Leu Ile Ser Gln Ala Val Phe Asn Gly Gly Arg
    50                  55                  60 cat gtc att ggg gtt atc ccc aag aca cta atg cca aga gag ata aca       240
His Val Ile Gly Val Ile Pro Lys Thr Leu Met Pro Arg Glu Ile Thr
65                  70                  75                  80 gga gag aca gtg gga gaa gtg aag gca gta gca gac atg cac caa agg       288
Gly Glu Thr Val Gly Glu Val Lys Ala Val Ala Asp Met His Gln Arg
                85                  90                  95 aaa gct gaa atg gct aag cac tct gat gct ttt atc gct tta cct ggt       336
Lys Ala Glu Met Ala Lys His Ser Asp Ala Phe Ile Ala Leu Pro Gly
            100                 105                 110 ggg tat ggg aca ctt gaa gag ctt ctt gaa gtt atc act tgg gca cag       384
Gly Tyr Gly Thr Leu Glu Glu Leu Leu Glu Val Ile Thr Trp Ala Gln
        115                 120                 125 cta ggc atc cat gat aaa cca gtg gga ctg ttg aat gtg gaa gga tac       432
Leu Gly Ile His Asp Lys Pro Val Gly Leu Leu Asn Val Glu Gly Tyr
    130                 135                 140 tac aat tca ttg tta tca ttc ata gac aaa gca gtg gaa gaa ggt ttc       480
Tyr Asn Ser Leu Leu Ser Phe Ile Asp Lys Ala Val Glu Glu Gly Phe
145                 150                 155                 160 att tca cca act gct cgt cat atc att gta tct gct cct tct gct aaa       528
Ile Ser Pro Thr Ala Arg His Ile Ile Val Ser Ala Pro Ser Ala Lys
                165                 170                 175 gaa ctt gtc aag aaa ctt gag gat tat gta cca agg cat gag aag gta       576
Glu Leu Val Lys Lys Leu Glu Asp Tyr Val Pro Arg His Glu Lys Val
            180                 185                 190 gcc tca aag aaa agc tgg gag atg gag caa ata ggg cta agt ccc act       624
Ala Ser Lys Lys Ser Trp Glu Met Glu Gln Ile Gly Leu Ser Pro Thr
        195                 200                 205 tgt gaa atc tca aga tga                                                642
Cys Glu Ile Ser Arg
    210
```

<210> SEQ ID NO 4
<211> LENGTH: 213
<212> TYPE: PRT
<213> ORGANISM: Arabidopsis sp.

<400> SEQUENCE: 4

```
Met Glu Ile Glu Ser Lys Phe Lys Arg Ile Cys Val Phe Cys Gly Ser
1               5                   10                  15

Ser Ala Gly Asn Lys Val Ser Tyr Lys Asp Ala Ala Ile Glu Leu Gly
            20                  25                  30
```

```
Thr Glu Leu Val Ser Arg Asn Ile Asp Leu Val Tyr Gly Gly Gly Ser
         35                  40                  45

Ile Gly Leu Met Gly Leu Ile Ser Gln Ala Val Phe Asn Gly Gly Arg
 50                  55                  60

His Val Ile Gly Val Ile Pro Lys Thr Leu Met Pro Arg Glu Ile Thr
 65                  70                  75                  80

Gly Glu Thr Val Gly Glu Val Lys Ala Val Ala Asp Met His Gln Arg
                 85                  90                  95

Lys Ala Glu Met Ala Lys His Ser Asp Ala Phe Ile Ala Leu Pro Gly
                100                 105                 110

Gly Tyr Gly Thr Leu Glu Glu Leu Leu Glu Val Ile Thr Trp Ala Gln
            115                 120                 125

Leu Gly Ile His Asp Lys Pro Val Gly Leu Leu Asn Val Glu Gly Tyr
130                 135                 140

Tyr Asn Ser Leu Leu Ser Phe Ile Asp Lys Ala Val Glu Glu Gly Phe
145                 150                 155                 160

Ile Ser Pro Thr Ala Arg His Ile Ile Val Ser Ala Pro Ser Ala Lys
                165                 170                 175

Glu Leu Val Lys Lys Leu Glu Asp Tyr Val Pro Arg His Glu Lys Val
            180                 185                 190

Ala Ser Lys Lys Ser Trp Glu Met Glu Gln Ile Gly Leu Ser Pro Thr
            195                 200                 205

Cys Glu Ile Ser Arg
210

<210> SEQ ID NO 5
<211> LENGTH: 642
<212> TYPE: DNA
<213> ORGANISM: Arabidopsis sp.
<220> FEATURE:
<221> NAME/KEY: CDS
<222> LOCATION: (1)..(642)

<400> SEQUENCE: 5 atg gaa gag aca aaa tca aga ttc agg agg atc tgt gtc ttc tgc gga      48
Met Glu Glu Thr Lys Ser Arg Phe Arg Arg Ile Cys Val Phe Cys Gly
 1               5                  10                  15 agc agt tcc ggc aac aaa acc act tat cac gac gct gct ctc caa ctc      96
Ser Ser Ser Gly Asn Lys Thr Thr Tyr His Asp Ala Ala Leu Gln Leu
             20                  25                  30 gcc cac caa ctg gtg gag aga aac atc gat ttg gtg tat gga gga gga     144
Ala His Gln Leu Val Glu Arg Asn Ile Asp Leu Val Tyr Gly Gly Gly
         35                  40                  45 agc gtg ggg cta atg ggt ctc att tct caa gct gtt cat gat ggt ggt     192
Ser Val Gly Leu Met Gly Leu Ile Ser Gln Ala Val His Asp Gly Gly
 50                  55                  60 cgt cat gtt ctt ggg atc att ccg aag tct cta gca cca aga gag ata     240
Arg His Val Leu Gly Ile Ile Pro Lys Ser Leu Ala Pro Arg Glu Ile
 65                  70                  75                  80 acc ggt gaa tca ata gga gaa gtt ata aca gta tcg act atg cac caa     288
Thr Gly Glu Ser Ile Gly Glu Val Ile Thr Val Ser Thr Met His Gln
                 85                  90                  95 agg aag gct gaa atg ggt cgc caa gcg gat gcc ttc atc gca ctt cct     336
Arg Lys Ala Glu Met Gly Arg Gln Ala Asp Ala Phe Ile Ala Leu Pro
                100                 105                 110 ggt gga tat ggg aca ttt gaa gag ttg ttg gaa gtc atc acc tgg tct     384
Gly Gly Tyr Gly Thr Phe Glu Glu Leu Leu Glu Val Ile Thr Trp Ser
            115                 120                 125 cag ctt ggg att cac act aaa ccg gtg gga cta ttg aac gtg gat gga     432
```

```
                                                                          -continued
Gln Leu Gly Ile His Thr Lys Pro Val Gly Leu Leu Asn Val Asp Gly
    130                 135                 140 ttc tac gat tca cta ttg acg ttt ata gat aag gca gtg gac gaa ggc     480
Phe Tyr Asp Ser Leu Leu Thr Phe Ile Asp Lys Ala Val Asp Glu Gly
145                 150                 155                 160 ttc gtc tcc tcc acc gct cgc cgt atc att gtc tcg gct cca aac gct     528
Phe Val Ser Ser Thr Ala Arg Arg Ile Ile Val Ser Ala Pro Asn Ala
                165                 170                 175 cct caa tta ctt caa ctt ctt gag gag tat gtt cca aaa cac gac gat     576
Pro Gln Leu Leu Gln Leu Leu Glu Glu Tyr Val Pro Lys His Asp Asp
            180                 185                 190 ttt gta tcc aaa atg gtg tgg gac aat acc acg gat gct ttc act ttg     624
Phe Val Ser Lys Met Val Trp Asp Asn Thr Thr Asp Ala Phe Thr Leu
        195                 200                 205 gaa ggc gac tcg ttt tag                                             642
Glu Gly Asp Ser Phe
    210

<210> SEQ ID NO 6
<211> LENGTH: 213
<212> TYPE: PRT
<213> ORGANISM: Arabidopsis sp.

<400> SEQUENCE: 6

Met Glu Glu Thr Lys Ser Arg Phe Arg Arg Ile Cys Val Phe Cys Gly
1               5                   10                  15

Ser Ser Ser Gly Asn Lys Thr Thr Tyr His Asp Ala Ala Leu Gln Leu
            20                  25                  30

Ala His Gln Leu Val Glu Arg Asn Ile Asp Leu Val Tyr Gly Gly Gly
        35                  40                  45

Ser Val Gly Leu Met Gly Leu Ile Ser Gln Ala Val His Asp Gly Gly
    50                  55                  60

Arg His Val Leu Gly Ile Ile Pro Lys Ser Leu Ala Pro Arg Glu Ile
65                  70                  75                  80

Thr Gly Glu Ser Ile Gly Glu Val Ile Thr Val Ser Thr Met His Gln
                85                  90                  95

Arg Lys Ala Glu Met Gly Arg Gln Ala Asp Ala Phe Ile Ala Leu Pro
            100                 105                 110

Gly Gly Tyr Gly Thr Phe Glu Glu Leu Leu Glu Val Ile Thr Trp Ser
        115                 120                 125

Gln Leu Gly Ile His Thr Lys Pro Val Gly Leu Leu Asn Val Asp Gly
    130                 135                 140

Phe Tyr Asp Ser Leu Leu Thr Phe Ile Asp Lys Ala Val Asp Glu Gly
145                 150                 155                 160

Phe Val Ser Ser Thr Ala Arg Arg Ile Ile Val Ser Ala Pro Asn Ala
                165                 170                 175

Pro Gln Leu Leu Gln Leu Leu Glu Glu Tyr Val Pro Lys His Asp Asp
            180                 185                 190

Phe Val Ser Lys Met Val Trp Asp Asn Thr Thr Asp Ala Phe Thr Leu
        195                 200                 205

Glu Gly Asp Ser Phe
    210

<210> SEQ ID NO 7
<211> LENGTH: 648
<212> TYPE: DNA
<213> ORGANISM: Arabidopsis sp.
<220> FEATURE:
<221> NAME/KEY: CDS
```

-continued

<210> LOCATION: (1)..(648)

<400> SEQUENCE: 7

```
atg gaa atc aaa ggt gaa tcg atg caa aag tca aag ttc aga aga atc      48
Met Glu Ile Lys Gly Glu Ser Met Gln Lys Ser Lys Phe Arg Arg Ile
1               5                   10                  15 tgt gtc ttc tgt gga agc agc caa ggc aag aag agc agt tac caa gat      96
Cys Val Phe Cys Gly Ser Ser Gln Gly Lys Lys Ser Ser Tyr Gln Asp
            20                  25                  30 gct gct gtt gac ctc ggc aac gaa ctg gtt tca agg aat att gat cta     144
Ala Ala Val Asp Leu Gly Asn Glu Leu Val Ser Arg Asn Ile Asp Leu
        35                  40                  45 gtc tat gga ggt ggg agc ata gga ttg atg ggt ttg gtt tca caa gct     192
Val Tyr Gly Gly Gly Ser Ile Gly Leu Met Gly Leu Val Ser Gln Ala
    50                  55                  60 gtt cat gat ggt ggt cgt cat gtt att gga atc att ccc aag acc ctc     240
Val His Asp Gly Gly Arg His Val Ile Gly Ile Ile Pro Lys Thr Leu
65                  70                  75                  80 atg cct aga gag ttg act ggt gaa aca gta gga gaa gta aga gca gtt     288
Met Pro Arg Glu Leu Thr Gly Glu Thr Val Gly Glu Val Arg Ala Val
                85                  90                  95 gca gat atg cac caa agg aaa gct gag atg gct aag cac tct gat gct     336
Ala Asp Met His Gln Arg Lys Ala Glu Met Ala Lys His Ser Asp Ala
            100                 105                 110 ttt att gcc tta cca ggt ggt tat gga aca ctt gaa gaa ttg ctt gaa     384
Phe Ile Ala Leu Pro Gly Gly Tyr Gly Thr Leu Glu Glu Leu Leu Glu
        115                 120                 125 gtc ata act tgg gct cag ctt ggt ata cat gac aag ccg gtg ggt ttg     432
Val Ile Thr Trp Ala Gln Leu Gly Ile His Asp Lys Pro Val Gly Leu
    130                 135                 140 ctc aat gtt gat gga tac tac aac tct ctg ctc tca ttc att gac aaa     480
Leu Asn Val Asp Gly Tyr Tyr Asn Ser Leu Leu Ser Phe Ile Asp Lys
145                 150                 155                 160 gca gtc gaa gaa gga ttt att agc ccg act gct cgt gag atc atc gtc     528
Ala Val Glu Glu Gly Phe Ile Ser Pro Thr Ala Arg Glu Ile Ile Val
                165                 170                 175 tcc gca cct act gct aaa gag ctg gtg aaa aag cta gag gaa tat gca     576
Ser Ala Pro Thr Ala Lys Glu Leu Val Lys Lys Leu Glu Glu Tyr Ala
            180                 185                 190 cct tgc cat gaa agg gtt gca acg aag ctt tgt tgg gag atg gaa cgg     624
Pro Cys His Glu Arg Val Ala Thr Lys Leu Cys Trp Glu Met Glu Arg
        195                 200                 205 att ggt tac tcc tct gaa gag tga                                     648
Ile Gly Tyr Ser Ser Glu Glu
    210                 215
```

<210> SEQ ID NO 8
<211> LENGTH: 215
<212> TYPE: PRT
<213> ORGANISM: Arabidopsis sp.

<400> SEQUENCE: 8

```
Met Glu Ile Lys Gly Glu Ser Met Gln Lys Ser Lys Phe Arg Arg Ile
1               5                   10                  15

Cys Val Phe Cys Gly Ser Ser Gln Gly Lys Lys Ser Ser Tyr Gln Asp
            20                  25                  30

Ala Ala Val Asp Leu Gly Asn Glu Leu Val Ser Arg Asn Ile Asp Leu
        35                  40                  45

Val Tyr Gly Gly Gly Ser Ile Gly Leu Met Gly Leu Val Ser Gln Ala
    50                  55                  60
```

```
Val His Asp Gly Gly Arg His Val Ile Gly Ile Ile Pro Lys Thr Leu
 65                  70                  75                  80

Met Pro Arg Glu Leu Thr Gly Glu Thr Val Gly Glu Val Arg Ala Val
                 85                  90                  95

Ala Asp Met His Gln Arg Lys Ala Glu Met Ala Lys His Ser Asp Ala
            100                 105                 110

Phe Ile Ala Leu Pro Gly Gly Tyr Gly Thr Leu Glu Glu Leu Leu Glu
        115                 120                 125

Val Ile Thr Trp Ala Gln Leu Gly Ile His Asp Lys Pro Val Gly Leu
    130                 135                 140

Leu Asn Val Asp Gly Tyr Tyr Asn Ser Leu Leu Ser Phe Ile Asp Lys
145                 150                 155                 160

Ala Val Glu Glu Gly Phe Ile Ser Pro Thr Ala Arg Glu Ile Ile Val
                165                 170                 175

Ser Ala Pro Thr Ala Lys Glu Leu Val Lys Lys Leu Glu Glu Tyr Ala
            180                 185                 190

Pro Cys His Glu Arg Val Ala Thr Lys Leu Cys Trp Glu Met Glu Arg
        195                 200                 205

Ile Gly Tyr Ser Ser Glu Glu
    210                 215

<210> SEQ ID NO 9
<211> LENGTH: 648
<212> TYPE: DNA
<213> ORGANISM: Arabidopsis sp.
<220> FEATURE:
<221> NAME/KEY: CDS
<222> LOCATION: (1)..(648)

<400> SEQUENCE: 9 atg gag gtc aac aat gaa acc atg caa aag tca aag ttt gga aga atc        48
Met Glu Val Asn Asn Glu Thr Met Gln Lys Ser Lys Phe Gly Arg Ile
1               5                   10                  15 tgt gtg ttt tgt gga agc agc caa ggc aag aag agt agt tac caa gat        96
Cys Val Phe Cys Gly Ser Ser Gln Gly Lys Lys Ser Ser Tyr Gln Asp
            20                  25                  30 gct gct gtg gat cta ggc aac gaa ttg gtt tta agg aac att gat cta       144
Ala Ala Val Asp Leu Gly Asn Glu Leu Val Leu Arg Asn Ile Asp Leu
        35                  40                  45 gtc tat gga ggt gga agc ata ggt ttg atg ggt ttg gtt tcg caa gct       192
Val Tyr Gly Gly Gly Ser Ile Gly Leu Met Gly Leu Val Ser Gln Ala
    50                  55                  60 gtt cat gat ggt ggt cgc cat gtt att gga gtt att ccc aag aca ctc       240
Val His Asp Gly Gly Arg His Val Ile Gly Val Ile Pro Lys Thr Leu
65                  70                  75                  80 atg cct aga gag ttg acc ggt gaa aca gta gga gaa gta aga gca gtt       288
Met Pro Arg Glu Leu Thr Gly Glu Thr Val Gly Glu Val Arg Ala Val
                85                  90                  95 gca gat atg cat caa aga aaa gca gag atg gct aga cac tct gat gct       336
Ala Asp Met His Gln Arg Lys Ala Glu Met Ala Arg His Ser Asp Ala
            100                 105                 110 ttt att gct tta cca ggt gga tat gga aca ctt gaa gag ctt ttg gag       384
Phe Ile Ala Leu Pro Gly Gly Tyr Gly Thr Leu Glu Glu Leu Leu Glu
        115                 120                 125 gtc ata aca tgg gct cag ctt gga ata cat gat aaa ccg gtg ggt ttg       432
Val Ile Thr Trp Ala Gln Leu Gly Ile His Asp Lys Pro Val Gly Leu
    130                 135                 140 ctc aat gtt gat gga tac tac aac tct ttg ctc tct ttc att gat aaa       480
Leu Asn Val Asp Gly Tyr Tyr Asn Ser Leu Leu Ser Phe Ile Asp Lys
145                 150                 155                 160
```

```
gcc gtt gaa gaa ggc ttc atc agt aca aac gca cgc cag atc ata att     528
Ala Val Glu Glu Gly Phe Ile Ser Thr Asn Ala Arg Gln Ile Ile Ile
            165                 170                 175 tct gca cct act gcc aag gag ctt gta aag aag ctg gag gaa tat tcg     576
Ser Ala Pro Thr Ala Lys Glu Leu Val Lys Lys Leu Glu Glu Tyr Ser
        180                 185                 190 cct tgc cat gaa agt gtt gcg act aag ctt tgt tgg gag ata gag cgg     624
Pro Cys His Glu Ser Val Ala Thr Lys Leu Cys Trp Glu Ile Glu Arg
        195                 200                 205 att gac tac tct tct gaa gac tga                                     648
Ile Asp Tyr Ser Ser Glu Asp
        210             215
```

<210> SEQ ID NO 10
<211> LENGTH: 215
<212> TYPE: PRT
<213> ORGANISM: Arabidopsis sp.

<400> SEQUENCE: 10

```
Met Glu Val Asn Asn Glu Thr Met Gln Lys Ser Lys Phe Gly Arg Ile
1               5                   10                  15

Cys Val Phe Cys Gly Ser Ser Gln Gly Lys Lys Ser Ser Tyr Gln Asp
            20                  25                  30

Ala Ala Val Asp Leu Gly Asn Glu Leu Val Leu Arg Asn Ile Asp Leu
        35                  40                  45

Val Tyr Gly Gly Gly Ser Ile Gly Leu Met Gly Leu Val Ser Gln Ala
    50                  55                  60

Val His Asp Gly Gly Arg His Val Ile Gly Val Ile Pro Lys Thr Leu
65                  70                  75                  80

Met Pro Arg Glu Leu Thr Gly Glu Thr Val Gly Glu Val Arg Ala Val
                85                  90                  95

Ala Asp Met His Gln Arg Lys Ala Glu Met Ala Arg His Ser Asp Ala
            100                 105                 110

Phe Ile Ala Leu Pro Gly Gly Tyr Gly Thr Leu Glu Glu Leu Leu Glu
        115                 120                 125

Val Ile Thr Trp Ala Gln Leu Gly Ile His Asp Lys Pro Val Gly Leu
    130                 135                 140

Leu Asn Val Asp Gly Tyr Tyr Asn Ser Leu Leu Ser Phe Ile Asp Lys
145                 150                 155                 160

Ala Val Glu Glu Gly Phe Ile Ser Thr Asn Ala Arg Gln Ile Ile Ile
                165                 170                 175

Ser Ala Pro Thr Ala Lys Glu Leu Val Lys Lys Leu Glu Glu Tyr Ser
            180                 185                 190

Pro Cys His Glu Ser Val Ala Thr Lys Leu Cys Trp Glu Ile Glu Arg
        195                 200                 205

Ile Asp Tyr Ser Ser Glu Asp
        210             215
```

<210> SEQ ID NO 11
<211> LENGTH: 687
<212> TYPE: DNA
<213> ORGANISM: Arabidopsis sp.
<220> FEATURE:
<221> NAME/KEY: CDS
<222> LOCATION: (1)..(687)

<400> SEQUENCE: 11

```
atg gaa ata gtg aag tcg agg ttc aag agg gtt tgt gtg ttc tgt ggt     48
Met Glu Ile Val Lys Ser Arg Phe Lys Arg Val Cys Val Phe Cys Gly
```

|  |  |  |  |  |  |  |  |  |  |  |  |  |  |  |  |
|---|---|---|---|---|---|---|---|---|---|---|---|---|---|---|---|
| 1 |  |  |  | 5 |  |  |  |  | 10 |  |  |  |  | 15 |  |

```
agc agc agc gga aag aga gag tgc tac agt gat gcc gcc act gat cta        96
Ser Ser Ser Gly Lys Arg Glu Cys Tyr Ser Asp Ala Ala Thr Asp Leu
                20                  25                  30 gct caa gag ctg gtg acg agg aga ttg aat ctt gtg tat gga gga gga       144
Ala Gln Glu Leu Val Thr Arg Arg Leu Asn Leu Val Tyr Gly Gly Gly
            35                  40                  45 agc att ggt ctc atg ggt ttg gtc tca caa gct gtt cat gaa gct gga       192
Ser Ile Gly Leu Met Gly Leu Val Ser Gln Ala Val His Glu Ala Gly
        50                  55                  60 gga cat gta cta ggg atc ata cca agg act ctt atg gac aaa gag ata       240
Gly His Val Leu Gly Ile Ile Pro Arg Thr Leu Met Asp Lys Glu Ile
65                  70                  75                  80 acc gga gaa aca tat ggt gag gta ata gct gtg gcg gat atg cat gaa       288
Thr Gly Glu Thr Tyr Gly Glu Val Ile Ala Val Ala Asp Met His Glu
                85                  90                  95 aga aaa gcc gaa atg gca cgc cac tcg gat tgt ttc att gct tta cca       336
Arg Lys Ala Glu Met Ala Arg His Ser Asp Cys Phe Ile Ala Leu Pro
            100                 105                 110 ggt ggg tat gga aca ctg gag gag tta ttg gaa gta ata gca tgg gca       384
Gly Gly Tyr Gly Thr Leu Glu Glu Leu Leu Glu Val Ile Ala Trp Ala
        115                 120                 125 caa ctt gga att cac gac aag cct gtg ggt ttg tta aat gtg gat ggt       432
Gln Leu Gly Ile His Asp Lys Pro Val Gly Leu Leu Asn Val Asp Gly
130                 135                 140 tat tac aat tac ctc ctc act ttc att gat aaa gcc gtt gat gat ggc       480
Tyr Tyr Asn Tyr Leu Leu Thr Phe Ile Asp Lys Ala Val Asp Asp Gly
145                 150                 155                 160 ttt atc aaa cca tct cag cgt cac atc ttt gtc tca gcc ccc aat gcc       528
Phe Ile Lys Pro Ser Gln Arg His Ile Phe Val Ser Ala Pro Asn Ala
                165                 170                 175 aaa gag ctt gtc caa aaa ctt gag gca tac aag cca gtg aat gat gga       576
Lys Glu Leu Val Gln Lys Leu Glu Ala Tyr Lys Pro Val Asn Asp Gly
            180                 185                 190 gtc ata gct aaa tct agg tgg gag gtt gag aag aaa gtg caa cag ccg       624
Val Ile Ala Lys Ser Arg Trp Glu Val Glu Lys Lys Val Gln Gln Pro
        195                 200                 205 caa caa cag caa caa gta gtg ttc tgt tct aac aca agc atg cag act       672
Gln Gln Gln Gln Gln Val Val Phe Cys Ser Asn Thr Ser Met Gln Thr
210                 215                 220 gag att gcc ctt tag                                                   687
Glu Ile Ala Leu
225

<210> SEQ ID NO 12
<211> LENGTH: 228
<212> TYPE: PRT
<213> ORGANISM: Arabidopsis sp.

<400> SEQUENCE: 12

Met Glu Ile Val Lys Ser Arg Phe Lys Arg Val Cys Val Phe Cys Gly
1               5                   10                  15

Ser Ser Ser Gly Lys Arg Glu Cys Tyr Ser Asp Ala Ala Thr Asp Leu
                20                  25                  30

Ala Gln Glu Leu Val Thr Arg Arg Leu Asn Leu Val Tyr Gly Gly Gly
            35                  40                  45

Ser Ile Gly Leu Met Gly Leu Val Ser Gln Ala Val His Glu Ala Gly
        50                  55                  60

Gly His Val Leu Gly Ile Ile Pro Arg Thr Leu Met Asp Lys Glu Ile
65                  70                  75                  80
```

```
Thr Gly Glu Thr Tyr Gly Glu Val Ile Ala Val Ala Asp Met His Glu
                85                  90                  95
Arg Lys Ala Glu Met Ala Arg His Ser Asp Cys Phe Ile Ala Leu Pro
            100                 105                 110
Gly Gly Tyr Gly Thr Leu Glu Glu Leu Leu Glu Val Ile Ala Trp Ala
        115                 120                 125
Gln Leu Gly Ile His Asp Lys Pro Val Gly Leu Leu Asn Val Asp Gly
    130                 135                 140
Tyr Tyr Asn Tyr Leu Leu Thr Phe Ile Asp Lys Ala Val Asp Asp Gly
145                 150                 155                 160
Phe Ile Lys Pro Ser Gln Arg His Ile Phe Val Ser Ala Pro Asn Ala
                165                 170                 175
Lys Glu Leu Val Gln Lys Leu Glu Ala Tyr Lys Pro Val Asn Asp Gly
            180                 185                 190
Val Ile Ala Lys Ser Arg Trp Glu Val Glu Lys Val Gln Gln Pro
        195                 200                 205
Gln Gln Gln Gln Gln Val Val Phe Cys Ser Asn Thr Ser Met Gln Thr
    210                 215                 220
Glu Ile Ala Leu
225

<210> SEQ ID NO 13
<211> LENGTH: 654
<212> TYPE: DNA
<213> ORGANISM: Arabidopsis sp.
<220> FEATURE:
<221> NAME/KEY: CDS
<222> LOCATION: (1)..(654)

<400> SEQUENCE: 13 atg gaa gag aca aaa tcg aga ttc aag agg atc tgt gtc ttc tgt gga    48
Met Glu Glu Thr Lys Ser Arg Phe Lys Arg Ile Cys Val Phe Cys Gly
1               5                   10                  15 agc agt tcc ggc aaa aaa cct tca tac caa gaa gct gcc att caa ttg    96
Ser Ser Ser Gly Lys Lys Pro Ser Tyr Gln Glu Ala Ala Ile Gln Leu
            20                  25                  30 ggt aac gag ttg gtg gag aga agg att gat ttg gta tac gga ggt ggt   144
Gly Asn Glu Leu Val Glu Arg Arg Ile Asp Leu Val Tyr Gly Gly Gly
        35                  40                  45 agc gtg ggg ctt atg ggt ctc gtc tct caa gct gtt cat cat ggt ggt   192
Ser Val Gly Leu Met Gly Leu Val Ser Gln Ala Val His His Gly Gly
    50                  55                  60 cgc cat gtt cta ggg gtc att cca aaa acc ttg atg cca aga gag ata   240
Arg His Val Leu Gly Val Ile Pro Lys Thr Leu Met Pro Arg Glu Ile
65                  70                  75                  80 act ggt gag acc atc gga gaa gtt aaa gcc gtg gcc gat atg cat caa   288
Thr Gly Glu Thr Ile Gly Glu Val Lys Ala Val Ala Asp Met His Gln
                85                  90                  95 agg aaa gct gaa atg gct cgc caa gcc gac gca ttc att gcc ctt cct   336
Arg Lys Ala Glu Met Ala Arg Gln Ala Asp Ala Phe Ile Ala Leu Pro
            100                 105                 110 ggt ggg tat ggt acg tta gaa gaa ttg ctg gaa gtc att aca tgg gct   384
Gly Gly Tyr Gly Thr Leu Glu Glu Leu Leu Glu Val Ile Thr Trp Ala
        115                 120                 125 caa ctc ggt atc cac cgt aag ccg gtg ggt ctt ctt aac gtg gat ggt   432
Gln Leu Gly Ile His Arg Lys Pro Val Gly Leu Leu Asn Val Asp Gly
    130                 135                 140 tac tac aac tcg ctg tta acg ttt att gat aag gct gtg gac gaa gga   480
Tyr Tyr Asn Ser Leu Leu Thr Phe Ile Asp Lys Ala Val Asp Glu Gly
```

```
                  145                 150                 155                 160
ttt ata tcc cca atg gct cgt cga atc atc gtc tca gct cca aac gct      528
Phe Ile Ser Pro Met Ala Arg Arg Ile Ile Val Ser Ala Pro Asn Ala
                165                 170                 175 aaa gag ttg gtt cga caa ctc gag gaa tat gaa ccg gag ttt gat gag      576
Lys Glu Leu Val Arg Gln Leu Glu Glu Tyr Glu Pro Glu Phe Asp Glu
            180                 185                 190 ata aca tca aaa ttg gtt tgg gat gaa gtg gac cgg ata agt tat gta      624
Ile Thr Ser Lys Leu Val Trp Asp Glu Val Asp Arg Ile Ser Tyr Val
            195                 200                 205 ccg ggt tcg gag gta gct acc gct acg taa                              654
Pro Gly Ser Glu Val Ala Thr Ala Thr
        210                 215

<210> SEQ ID NO 14
<211> LENGTH: 217
<212> TYPE: PRT
<213> ORGANISM: Arabidopsis sp.

<400> SEQUENCE: 14

Met Glu Glu Thr Lys Ser Arg Phe Lys Arg Ile Cys Val Phe Cys Gly
1               5                   10                  15

Ser Ser Ser Gly Lys Lys Pro Ser Tyr Gln Glu Ala Ala Ile Gln Leu
            20                  25                  30

Gly Asn Glu Leu Val Glu Arg Arg Ile Asp Leu Val Tyr Gly Gly Gly
        35                  40                  45

Ser Val Gly Leu Met Gly Leu Val Ser Gln Ala Val His His Gly Gly
    50                  55                  60

Arg His Val Leu Gly Val Ile Pro Lys Thr Leu Met Pro Arg Glu Ile
65                  70                  75                  80

Thr Gly Glu Thr Ile Gly Glu Val Lys Ala Val Ala Asp Met His Gln
                85                  90                  95

Arg Lys Ala Glu Met Ala Arg Gln Ala Asp Ala Phe Ile Ala Leu Pro
            100                 105                 110

Gly Gly Tyr Gly Thr Leu Glu Glu Leu Leu Glu Val Ile Thr Trp Ala
        115                 120                 125

Gln Leu Gly Ile His Arg Lys Pro Val Gly Leu Leu Asn Val Asp Gly
    130                 135                 140

Tyr Tyr Asn Ser Leu Leu Thr Phe Ile Asp Lys Ala Val Asp Glu Gly
145                 150                 155                 160

Phe Ile Ser Pro Met Ala Arg Arg Ile Ile Val Ser Ala Pro Asn Ala
                165                 170                 175

Lys Glu Leu Val Arg Gln Leu Glu Glu Tyr Glu Pro Glu Phe Asp Glu
            180                 185                 190

Ile Thr Ser Lys Leu Val Trp Asp Glu Val Asp Arg Ile Ser Tyr Val
            195                 200                 205

Pro Gly Ser Glu Val Ala Thr Ala Thr
        210                 215

<210> SEQ ID NO 15
<211> LENGTH: 651
<212> TYPE: DNA
<213> ORGANISM: Arabidopsis sp.
<220> FEATURE:
<221> NAME/KEY: CDS
<222> LOCATION: (1)..(651)

<400> SEQUENCE: 15 atg gaa gat aat cag cga agc aga ttc aga aaa atc tgt gtc ttt tgc      48
```

```
Met Glu Asp Asn Gln Arg Ser Arg Phe Arg Lys Ile Cys Val Phe Cys
1               5                   10                  15 gga agc cac tct ggt cac aga gaa gtt ttc agt gat gct gcc atc gaa        96
Gly Ser His Ser Gly His Arg Glu Val Phe Ser Asp Ala Ala Ile Glu
            20                  25                  30 ctc ggc aat gaa ctc gtg aag agg aag ata gat ttg gtt tat gga gga       144
Leu Gly Asn Glu Leu Val Lys Arg Lys Ile Asp Leu Val Tyr Gly Gly
        35                  40                  45 gga agt gtt gga ttg atg ggt ttg ata tcc agg aga gtc tat gaa ggt       192
Gly Ser Val Gly Leu Met Gly Leu Ile Ser Arg Arg Val Tyr Glu Gly
    50                  55                  60 ggt tta cat gta ctt gga atc att ccc aaa gct ttg atg cca att gag       240
Gly Leu His Val Leu Gly Ile Ile Pro Lys Ala Leu Met Pro Ile Glu
65                  70                  75                  80 ata tct ggt gag act gtg gga gat gta aga gtt gtt gca gac atg cat       288
Ile Ser Gly Glu Thr Val Gly Asp Val Arg Val Val Ala Asp Met His
                85                  90                  95 gag cga aag gct gca atg gca cag gaa gct gag gcc ttc att gca ctc       336
Glu Arg Lys Ala Ala Met Ala Gln Glu Ala Glu Ala Phe Ile Ala Leu
            100                 105                 110 cct gga ggt tat gga aca atg gag gag ctg ttg gag atg ata aca tgg       384
Pro Gly Gly Tyr Gly Thr Met Glu Glu Leu Leu Glu Met Ile Thr Trp
        115                 120                 125 tca caa ctt ggt atc cat aag aag acg gtt ggt cta ttg aat gtt gat       432
Ser Gln Leu Gly Ile His Lys Lys Thr Val Gly Leu Leu Asn Val Asp
    130                 135                 140 ggg tac tat aac aat ttg ctt gct tta ttt gat acc ggt gtc gaa gaa       480
Gly Tyr Tyr Asn Asn Leu Leu Ala Leu Phe Asp Thr Gly Val Glu Glu
145                 150                 155                 160 ggt ttt atc aag cca ggt gca cgt aac att gtg gtt tct gct cca aca       528
Gly Phe Ile Lys Pro Gly Ala Arg Asn Ile Val Val Ser Ala Pro Thr
                165                 170                 175 gcc aaa gag ctt atg gag aag atg gag gaa tat act cct tca cac atg       576
Ala Lys Glu Leu Met Glu Lys Met Glu Glu Tyr Thr Pro Ser His Met
            180                 185                 190 cat gtt gca tcg cac gaa agc tgg aaa gtt gaa gaa ctc gga gat tac       624
His Val Ala Ser His Glu Ser Trp Lys Val Glu Glu Leu Gly Asp Tyr
        195                 200                 205 ccg gga caa gaa aac aag ccg caa taa                                   651
Pro Gly Gln Glu Asn Lys Pro Gln
    210                 215

<210> SEQ ID NO 16
<211> LENGTH: 216
<212> TYPE: PRT
<213> ORGANISM: Arabidopsis sp.

<400> SEQUENCE: 16

Met Glu Asp Asn Gln Arg Ser Arg Phe Arg Lys Ile Cys Val Phe Cys
1               5                   10                  15

Gly Ser His Ser Gly His Arg Glu Val Phe Ser Asp Ala Ala Ile Glu
            20                  25                  30

Leu Gly Asn Glu Leu Val Lys Arg Lys Ile Asp Leu Val Tyr Gly Gly
        35                  40                  45

Gly Ser Val Gly Leu Met Gly Leu Ile Ser Arg Arg Val Tyr Glu Gly
    50                  55                  60

Gly Leu His Val Leu Gly Ile Ile Pro Lys Ala Leu Met Pro Ile Glu
65                  70                  75                  80

Ile Ser Gly Glu Thr Val Gly Asp Val Arg Val Val Ala Asp Met His
                85                  90                  95
```

```
Glu Arg Lys Ala Ala Met Ala Gln Glu Ala Glu Ala Phe Ile Ala Leu
            100             105             110

Pro Gly Gly Tyr Gly Thr Met Glu Glu Leu Leu Glu Met Ile Thr Trp
            115             120             125

Ser Gln Leu Gly Ile His Lys Lys Thr Val Gly Leu Leu Asn Val Asp
            130             135             140

Gly Tyr Asn Asn Leu Leu Ala Leu Phe Asp Thr Gly Val Glu Glu
145             150             155             160

Gly Phe Ile Lys Pro Gly Ala Arg Asn Ile Val Val Ser Ala Pro Thr
            165             170             175

Ala Lys Glu Leu Met Glu Lys Met Glu Glu Tyr Thr Pro Ser His Met
            180             185             190

His Val Ala Ser His Glu Ser Trp Lys Val Glu Glu Leu Gly Asp Tyr
            195             200             205

Pro Gly Gln Glu Asn Lys Pro Gln
            210             215
```